(12) United States Patent
Dhaliwal et al.

(10) Patent No.: US 11,180,630 B2
(45) Date of Patent: Nov. 23, 2021

(54) METAL SALTS OF MALONIC ACID AS NUCLEATING ADDITIVES FOR CRYSTALLINE THERMOPLASTICS

(71) Applicant: INDIAN OIL CORPORATION LIMITED, Mumbai (IN)

(72) Inventors: Jatinder Singh Dhaliwal, Faridabad (IN); Vishal Goel, Faridabad (IN); Bhasker Bantu, Faridabad (IN); Sameeksha Raizada, Faridabad (IN); Shiva Naresh, Faridabad (IN); Vimal Kakkarakkal Kottiyath, Faridabad (IN); Raja Poddar, Panipat (IN); Gurpreet Singh Kapur, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 11 days.

(21) Appl. No.: 16/237,288

(22) Filed: Dec. 31, 2018

(65) Prior Publication Data

US 2019/0256683 A1    Aug. 22, 2019

(30) Foreign Application Priority Data

Feb. 20, 2018    (IN) .............................. 201821006440

(51) Int. Cl.
| C08K 5/098 | (2006.01) |
| C08L 23/02 | (2006.01) |
| C07C 51/41 | (2006.01) |
| C08K 3/22 | (2006.01) |
| C08K 5/00 | (2006.01) |

(52) U.S. Cl.
CPC ............ *C08K 5/098* (2013.01); *C07C 51/418* (2013.01); *C08K 3/22* (2013.01); *C08L 23/02* (2013.01); *C07C 51/41* (2013.01); *C08K 5/0083* (2013.01); *C08K 2003/2296* (2013.01); *C08L 2205/24* (2013.01)

(58) Field of Classification Search
CPC ........ C08K 5/098; C08K 3/22; C08K 5/0083; C08K 2003/2296; C07C 51/418; C07C 51/41; C08L 23/02; C08L 2205/24
USPC ....................................................... 524/400
See application file for complete search history.

(56) References Cited

U.S. PATENT DOCUMENTS

| 3,207,735 | A | 9/1965 | Wigja |
| 3,207,737 | A | 9/1965 | Wales et al. |
| 3,299,029 | A | 1/1967 | Binsbergen et al. |
| 3,326,880 | A | 6/1967 | Binsbergen et al. |
| 3,327,020 | A | 6/1967 | Binsbergen |
| 3,359,344 | A | 12/1967 | Fukushima et al. |
| 3,639,505 | A | 2/1972 | Hughes et al. |
| 3,900,549 | A | 8/1975 | Yamane et al. |
| 4,359,557 | A | 11/1982 | Watkins et al. |
| 4,410,473 | A | 10/1983 | Iohara et al. |
| 4,454,196 | A | 6/1984 | Iohara et al. |
| 4,559,862 | A | 12/1985 | Case et al. |
| 4,562,869 | A | 1/1986 | Blum |
| 4,567,092 | A | 1/1986 | Catrain et al. |
| 4,587,154 | A | 5/1986 | Hotchkiss et al. |
| 4,609,710 | A | 9/1986 | Iohara et al. |
| 5,231,126 | A | 7/1993 | Shi et al. |
| 7,552,603 | B2 | 6/2009 | Dahlgren |
| 2008/0282930 | A1* | 11/2008 | Notoya ................. C09D 11/38 106/31.6 |
| 2010/0010168 | A1 | 1/2010 | Wolfschwenger et al. |
| 2010/0016603 | A1* | 1/2010 | Sonoda ................ C07D 213/64 546/250 |

FOREIGN PATENT DOCUMENTS

| DE | 3610644 A1 | 10/1986 |
| EP | 0177961 A2 | 4/1986 |
| EP | 0682066 A1 | 11/1995 |

OTHER PUBLICATIONS

Delarbre et al., "Analyse Vibrationnelle et Structurale en Sére Aliphatic Saturée—4†—Spectres de Vibration de l'Acide Diméthylmalonique etdeses Seis Alcalins en Solution Aqueuse," J. Raman Spectroscopy, vol. 13, No. 1, pp. 1-8. (Year: 1982).*
Delabre al., "Analyse Vibrationnelle et Structurale en Sére Aliphatic Saturée—5†—Spectres de Vibration de l'Acide Éthylmalonique et de ses Seis Alcalins en Solution Aqueuse," J. Raman Spectroscopy, vol. 14, No. 6, pp. 426-433. (Year: 1983).*
Kovalenko et al., "Possibility of preparation ofvolataile compounds of metals with ligands—derivative of malonic acid," Vestnik Moskovskogo Universiteta, Seriya 2: Khimya, vol. 33, No. 5, pp. 476-482, ISSN: 0579-9384, SciFinder abstract. (Year: 1992).*
Li et al., "Effect of Metallic Salts of Phenylmalonic Acid on the Crystallization of Poly(L-lactide)," J. Macromol. Sci. B, vol. 55, No. 2, 128-137. (Year: 2016).*
Driscoll et al., "Polyelectrolyte Membranes Containing Lithium Malonato(difluoro)borate for Lithium-Ion Systems," ECS Trans., 33(23), 33-53. (Year: 2011).*
Beck, N., H., and Ledbetter, D., H., "DTA study of heterogeneous nucleation of crystallization in polypropylene†," Applied Polymer Science, vol. 9, Issue 6, pp. 2131-2142 (Jun. 1965).

(Continued)

*Primary Examiner* — Josephine L Chang
(74) *Attorney, Agent, or Firm* — Maschoff Brennan

(57) ABSTRACT

The present invention provides a metal salt of malonic acid derivative compound having chemical formula (I) as an α-nucleating agent and process for preparing the same. The present invention also provides a polymer additive and thermoplastic composition comprising the metal salt of malonic acid derivative compound having chemical formula (I).

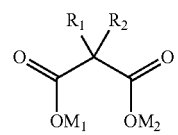

I

10 Claims, No Drawings

(56) References Cited

OTHER PUBLICATIONS

Beck, N., H., "Heterogeneous nucleating agents for polypropylene crystallization," Applied Polymer Science, vol. 11, Issue 5, pp. 673-685 (1967).
Binsbegen, L., F., "Heterogeneous nucleation in the crystallization of polyolefins: Part 1. Chemical and physical nature of nucleating agents," Polymer, vol. 11, Issue 5, pp. 253-267 (May 1970).

* cited by examiner

METAL SALTS OF MALONIC ACID AS NUCLEATING ADDITIVES FOR CRYSTALLINE THERMOPLASTICS

FIELD OF THE INVENTION

The present invention relates to compounds and compositions comprising metal salts of Malonic acid derivatives. These metal salts of malonic acid derivatives are useful as α-nucleating agents to improve properties of thermoplastic polymers or articles. The compounds (metal salts of malonic acid derivatives) provide higher crystallization temperature and stiffness with low hygroscopicity when used in thermoplastic and their formulations.

BACKGROUND OF THE INVENTION

Nucleating agents are used in polymer resin to manufacture of plastic articles by various methods, including by injection or extrusion molding. It helps to achieve a polymer significant cycle time reduction in the molding process compared to using non nucleated polymer. Cycle time reduction can be achieved in molded part by inducing in the resin a higher Tc (crystallization temperature). This decreases the necessary cooling time and facilitates ejection of the articles from the mold at a faster rate than would be possible without the use of alpha nucleating agents. Another class of nucleating agents used specifically for polypropylene is the β-nucleating agent. These compounds lead to increase in impact strength, lower melting temperature and possibility of altogether different set of applications.

EP0177961 discloses the process by which β-modification is achieved by shear induced crystallization or by crystallization under temperature gradient or by adding specific β-nucleating agents, such as quinacridone pigments. U.S. Pat. No. 5,231,126 and DE 3610644 disclose two component type beta nucleating agent and it consisted of a mixture of an organic dibasic acid, such as malonic acid, pimelic acid, azelaic acid, o-phthalic acid, terephthalic and isophthalic acid with an oxide, hydroxide or acid salt of a Group II metal e.g. magnesium, Calcium, Strontium etc. which when employed in Polypropylene matrix gave beta crystalline structure. EP0682066 describes synthesis process for one component β-nucleating agent, produced by reacting 1 mol of dicarboxylic acid with 1 mol calcium carbonate in an aqueous ethanol containing solution at 60° C.–80° C. US2010/0010168 provides a process for preparation of β-nucleating agent. Process involves treating mixture comprising a dibasic organic acid and an oxide, hydroxide or acid salt of group II metal at a temperature above 120° C.

The material that softens when heated above the glass transition temperature or melting temperature and becomes hard after cooling is called thermoplastics. Thermoplastics can be reversibly melted by heating and solidified by cooling in limited number of cycles without affecting the mechanical properties. On increasing the number of recycling of thermoplastics may result in color degradation, thereby affecting their appearance and properties. In the molten state, they are liquids, and in the mushy state they are glassy or partially crystalline. The molecules are joined end-to-end into a series of long chains, each chain being independent of the other. Above the melting temperature, all crystalline structure disappears and the long chain becomes randomly scattered.

The molecular structure of thermoplastic has an influence on the chemical resistance and resistance against environmental effects like UV radiation. The properties may also vary from optical transparency to opaque, depending on the molecular structure. The important properties of the thermoplastics are high strength and toughness, better hardness, chemical resistance, durability, self lubrication, transparency and water proofing. With the application of heat, thermoplastic softens and it can be molded into desired shapes. Some thermoplastics can be joined with the application of heat and pressure. There are several techniques available for the joining of thermoplastics such as mechanical fastening, fusion bonding, hot gas welding, solvent bonding, ultrasonic welding, induction welding, and dielectric welding.

The different types of thermoplastic are selected from Acrylonitrile Butadiene Styrene (ABS), Acetal, Acrylic, Cellulosic, Fluorocarbon, Polyamide, Polycarbonate, Polyethylene (PE), Polypropylene (PP), Polystyrene, Polyetherketone, Polyvinyl Chloride (PVC), Liquid Crystal Polymer (LCP), Polyphenylene Sulphide (PPS) and Vinyl.

Polyolefin family of polymers derived from a particular group of base materials known as olefins, are the world's fastest growing polymer family. Polyolefins such as polyethylene (PE) and polypropylene (PP) are commodity plastics found in applications varying from house hold items such as grocery bags, containers, carpets, toys and appliances, to high tech products such as engineering plastics, industrial pipes, automotive parts, medial appliances and even prosthetic implants.

The process of manufacturing of Polyolefins, namely polyethylene (PE) and polypropylene (PP), involves use of various additives such as antioxidants, heat stabilizers, UV stabilizers, acid scavengers, antistatic agents, or any other additive to maintain or enhance the performance of the final polymer. In addition to this specialty additives are used such as crystallinity modifiers which further augment some of the properties of the resin such as increase in clarity of polymers, cycle time reduction by way of increasing the crystallization temperature (Tc) or lowering the polymer melting temperatures (Tm) thereby broadening the processing window of especially semi crystalline polyolefin polymers. This type of property of a polyolefin polymer increases its application areas and processor can make niche products.

Crystallization is a process in which the molten polymer is cooled below its melting temperature such that the crystalline order begins to reestablish. Crystallization occurs essentially in two stages, nucleation and crystal growth. Nucleation is a process in which the loose coiled polymer chains orient themselves into the proper conformation and align into a perfect three-dimensional pattern. The site at which the nucleation starts is called the nucleus. During crystal growth polymer chains orient to the three-dimensional pattern on the nucleus and mostly form a spherical crystal cluster which is called a spherulite. Nucleation in polymers may be homogeneous or heterogeneous. Homogeneous nucleation occurs at high super-cooling in pure polymers. Heterogeneous nucleation occurs at relatively low super-cooling, when a foreign body is present in the melt which reduces the free energy barrier for nucleation. These foreign bodies are called nucleating agents or nucleators.

A third kind of nucleation called self-nucleation also occurs in polymer crystallization which is caused due to the presence of partially melted polymer, which acts as a nucleus. Nucleators raise the crystallization temperature. They also shorten time required for crystallization, thus reducing the cycle time in injection molding processes. Nucleators increase the number of crystallization sites in a polymer thus reducing the spherulite size. They cause simultaneous growth and thus evenly sized crystals. Smaller evenly sized crystals improve the physical properties of the polymers like transparency, surface gloss and impact strength.

As an example, dibenzylidene sorbitol derivatives are common nucleator compounds, particularly for polypropylene end-products. Compounds such as 1,3-O-2,4-bis(3,4dimethylbenzylidene) sorbitol (hereinafter DMDBS), available from Milliken Chemical under the trade name Millad®3988, provide excellent nucleation and clarification characteristics for target polypropylenes and other polyolefin. Other well-known nucleator compounds include sodium benzoate, sodium 2,2'-methylene-bis-(4,6-di-tert-butylphenyl) phosphate (from Asahi Denka Kogyo K.K., known as NA-11), aluminum bis[2,2'-methylene-bis-(4,6-di-tert-butylphenyl)phosphate] (also from Asahi Denka Kogyo K.K., known as NA-21), talc, and the like. Such compounds all impart high polyolefin crystallization temperatures; however, each also exhibits its own drawback for large-scale industrial applications.

Nucleation by foreign materials has been extensively studied, especially in the case of polypropylene. For example, H. N. Beck or H. D. Led better, J. Appl. Polym. Sci. 9, 2131 (1965) and H. N. Beck, J. Appl Polym. Sci. 11,673 (1987) checked the nucleation activity of more than two hundred substances by determining the temperature, Tc, at which the crystallization rate on cooling is the fastest. F. L. Binsbergen, Polymer, 11, 253 (1970) extended these studies in testing two thousand substances for nucleating activity in polyethylene, polypropylene, poly(4-methyl-1-pentene) and poly(styrene). Other working nucleating agents for polyolefin are described on the patent literatures i.e., U.S. Pat. Nos. 3,207,735, 3,299,029, 3,207,737, 3,326,880, 3,327,020.

The patent literatures namely U.S. Pat. Nos. 4,454,196, 4,410,473, 4,359,557, 4,587,154, 4,567,092, 4,562,869, 4,559,862 discloses Polyesters and poly-olefinic materials and have experienced acceptance in forming shaped objects, as for example films, sheets, fibers and the like.

Mixture of polyolefin's and polyesters and the use of same to fabricate articles such as film and fibers are known in the patent literatures namely U.S. Pat. Nos. 3,639,505, 4,609,710, 3,900,549, 3,359,344 and 7,552,603.

Some of the common issues/problems encountered in the above discussed prior arts are listed as below:
1. Compatibility:—Compatibility of these compounds in polyolefin (e.g. Polypropylene, polyethylene, and the like thermoplastics) is of great interest since many different additives are being used. Typical formulations in Polyolefin material consists of stabilizing additives (e.g. light stabilizers, antioxidants, etc.), acid neutralizers (e.g. calcium stearate, zinc stearate, hydrotalcites, etc.) etc. Unfortunately most of the known nucleating compounds mentioned above exhibit deleterious reactions with certain additives like metal stearates leading to reduced nucleation performance of intended compounds or other processing problems.
2. Dispersion:—Another problem faced with the nucleators is inconsistent nucleation due to dispersion problems in polymer matrix which results in variation in the stiffness, impact and finish of polyolefin article made thereof.
3. Storage:—Most of the nucleator compounds are provided or supplied in powder or granular form to resin manufacturers. Nucleators such as sodium benzoate exhibit high degree of hydroscopicity which leads to agglomeration of the particles. Such type of agglomerated particles results into feeding issues, handling issues, poor dispersion in polyolefin material and polyolefin article having lower stiffness or impact or both. Agglomerated articles have to be subjected to further drying and milling process leading to increase in economics.

Objectives of the Invention

The present invention overcomes all the limitations listed above and is to provide a nucleator compound and compositions thereof which exhibits excellent compatibility with known additives used in polyolefins (e.g. polypropylene, polyethylene, and the like thermoplastics), excellent high peak crystallization temperature, extremely low hygroscopicity, easily dispersed nucleator compound in at said polyolefins.

It is an objective of the present invention is to provide compounds and compositions comprising metal salts of malonic acid derivatives in order to improve properties of thermoplastic polymers or articles. These compounds get easily dispersed in polymer matrix thus providing higher crystallization temperature, stiffness and good clarity with very low hygroscopicity.

Advantages of the Invention

The present invention as summarized above holds many advantages to the existing prior art:
No compatibility issues
No dispersion problems
Low hygroscopicity
No complicated synthesis steps involved in modification

SUMMARY OF THE INVENTION

Accordingly the present invention provides a metal salt of malonic acid derivative compound having formula (I) as an α-nucleating agent:

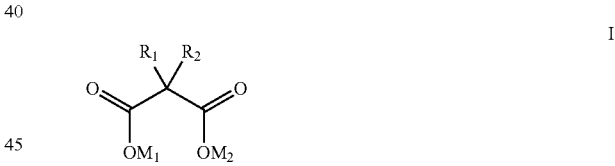

wherein:
each of $R_1$ and $R_2$ groups are independently selected from the group consisting of hydrogen, alkyl, aryl, alkyl aryl, halogen and cycloalkyl, provided that $R_1$ and $R_2$ are not both hydrogen; and each of $M_1$ and $M_2$ are selected from monovalent metal and divalent metal.

The present invention also provides a process for preparing a metal salt of malonic acid derivative, wherein the process comprising adding a malonic acid derivative in water and metal hydroxide to obtain a reaction mixture slurry and then heating the reaction mixture slurry along with continuous stirring to obtain a metal salt of malonic acid derivative.

The present invention also provides a polymer additive comprising:
(i) a component selected from metal stearate, metal oxide, and mixture thereof; and
(ii) the metal salt of malonic acid derivative compound having formula (I).

The present invention also provides a thermoplastic composition comprising;
(i) a polyolefin resin or polyolefin formulation; and
(ii) the metal salt of malonic acid derivative compound having formula (I).

DETAILED DESCRIPTION OF THE INVENTION

Accordingly present invention provides a metal salt of malonic acid derivative compound confirming to formula (I) as an α-nucleating agent. The metal salts of malonic acid derivative compounds are represented by chemical Formula (I):

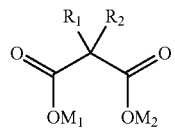

I wherein:
each of $R_1$ and $R_2$ groups are independently selected from hydrogen, alkyl, aryl, alkyl aryl, halogen and cycloalkyls; provided that $R_1$ and $R_2$ are not both hydrogen, and each of $M_1$ and $M_2$ are selected from monovalent metal, and divalent metal.

In one of the feature of the present invention, monovalent metal is selected from lithium, sodium, and potassium, and divalent metal is selected from barium, calcium and magnesium.

In one of the feature of the present invention, $M_1$ and $M_2$ are same metal. In another feature of the present invention $M_1$ and $M_2$ are not same metal.

In another feature of the present invention, wherein each $R_1$ and $R_2$ are independently selected from hydrogen, halogen, alkyl having 1 to about 14 carbon atoms, phenyl, arylalkyl having 6 to about 18 carbon atoms or alkyl aryl having 7 to 18 carbon atoms, provided that $R_1$ and $R_2$ are not both hydrogen. In one of the feature of the present invention alkyl aryl is selected from ethyl phenyl, propyl phenyl, iso propyl phenyl, tert-butyl phenyl, benzyl or like.

In one of the feature of the present invention, the compound of formula I is selected from the group consisting of sodium 2,2-dimethylmalonate, sodium 2,2-diethylmalonate, sodium 2,2-dipropylmalonate, sodium 2,2-dibutylmalonate, sodium 2,2-dipentylmalonate, sodium 2,2-dihexylmalonate, sodium 2,2-diheptylmalonate, sodium 2,2-dioctylmalonate, sodium 2,2-dinonylmalonate, sodium 2,2-didecylmalonate, sodium 2,2-diundecylmalonate, sodium 2,2-didodecylmalonate, sodium 2-dodecyl-2-undecylmalonate, sodium 2-decyl-2-dodecylmalonate, sodium 2-dodecyl-2-nonylmalonate, sodium 2-dodecyl-2-octylmalonate, sodium 2-dodecyl-2-heptylmalonate, sodium 2-dodecyl-2-hexylmalonate, sodium 2-dodecyl-2-pentylmalonate, sodium 2-butyl-2-dodecylmalonate, sodium 2-dodecyl-2-propylmalonate, sodium 2-dodecyl-2-ethylmalonate, sodium 2-dodecyl-2-methylmalonate, sodium 2-dodecylmalonate, sodium 2-undecylmalonate, sodium 2-decylmalonate, sodium 2-nonylmalonate, sodium 2-octylmalonate, sodium 2-heptylmalonate, sodium 2-hexylmalonate, sodium 2-pentylmalonate, sodium 2-butylmalonate, sodium 2-propylmalonate, sodium 2-ethylmalonate, sodium 2-methylmalonate, sodium 2-phenylmalonate, sodium 2-(p-tolyl)malonate, sodium 2-mesitylmalonate, sodium 2-(4-(tert-butyl)phenyl) malonate, sodium 2-(4-(tert-butyl)-2-methylphenyl)malonate, sodium 2-(4-(tert-butyl)-2,6-dimethylphenyl)malonate, sodium 2,2-diphenylmalonate, sodium 2-methyl-2-phenylmalonate, sodium 2-ethyl-2-phenylmalonate, sodium 2-phenyl-2-propylmalonate, sodium 2-butyl-2-phenylmalonate, sodium 2-pentyl-2-phenylmalonate, sodium 2-hexyl-2-phenylmalonate, sodium 2-heptyl-2-phenylmalonate, sodium 2-octyl-2-phenylmalonate, sodium 2-nonyl-2-phenylmalonate, sodium 2-decyl-2-phenylmalonate, sodium 2-phenyl-2-undecylmalonate, sodium 2-dodecyl-2-phenylmalonate, sodium 2-isopropyl-2-methylmalonate, sodium 2,2-diisopropylmalonate, sodium 2-isopropylmalonate, sodium 2-(tert-butyl)malonate, sodium 2-ditert-butylmalonate, sodium 2-(tert-butyl)-2-methylmalonate, sodium 2-(tert-butyl)-2-ethylmalonate, sodium 2-ethyl-2-isopropylmalonate, sodium 2-isopropyl-2-propylmalonate, sodium 2-butyl-2-isopropylmalonate, sodium 2-isopropyl-2-pentylmalonate, sodium 2-hexyl-2-isopropylmalonate, sodium 2-heptyl-2-isopropylmalonate, sodium 2-isopropyl-2-octylmalonate, sodium 2-isopropyl-2-nonylmalonate, sodium 2-decyl-2-isopropylmalonate, sodium 2-isopropyl-2-undecylmalonate, sodium 2-(tert-butyl)-2-undecylmalonate, sodium 2-(tert-butyl)-2-decylmalonate, sodium 2-(tert-butyl)-2-nonylmalonate, sodium 2-(tert-butyl)-2-octylmalonate, sodium 2-(tert-butyl)-2-heptylmalonate, sodium 2-(tert-butyl)-2-hexylmalonate, sodium 2-(tert-butyl)-2-pentylmalonate, sodium 2-(tert-butyl)-2-butylmalonate, sodium 2-(tert-butyl)-2-propylmalonate, sodium 2-(tert-butyl)-2-ethylmalonate, sodium 2-(tert-butyl)-2-phenylmalonate, sodium 2-isopropyl-2-phenylmalonate, sodium 2-(sec-butyl)malonate, sodium 2-(sec-butyl)-2-methylmalonate, sodium 2-methyl-2-(pentan-2-yl)malonate, sodium 2-(hexan-2-yl)-2-methylmalonate, sodium 2-(heptan-2-yl)-2-methylmalonate, sodium 2-methyl-2-(octan-2-yl)malonate, sodium 2-methyl-2-(nonan-2-yl)malonate, sodium 2-methyl-2-(octan-3-yl)malonate, sodium 2-(octan-3-yl)-2-octylmalonate, sodium 2-benzyl-2-methylmalonate, sodium 2,2-dibenzylmalonate, sodium 2-benzyl-2-ethylmalonate, sodium 2-benzyl-2-isopropylmalonate, sodium 2-benzyl-2-(tert-butyl)malonate, sodium 2-cyclohexylmalonate, sodium 2-cyclohexyl-2-methylmalonate, sodium 2-cyclohexyl-2-ethylmalonate, sodium 2-cyclohexyl-2-isopropylmalonate, sodium 2-(tert-butyl)-2-cyclohexylmalonate, sodium 2,2-dicyclohexylmalonate, sodium 2-cyclohexyl-2-(pentan-3-yl) malonate, sodium 2-ethylmalonate, sodium 2-isopropylmalonate, sodium 2-(tert-butyl)malonate, sodium 2-propylmalonate, sodium 2-butylmalonate, sodium 2-pentylmalonate, sodium 2-(2-methylpentyl)malonate, sodium 2-(2-ethylpentyl)malonate, sodium 2-(3-ethylhexan-2-yl) malonate, sodium 2-hexylmalonate, sodium 2-heptylmalonate, sodium 2-octylmalonate, sodium 2-nonylmalonate, sodium 2-decylmalonate, sodium 2-decyl-2-isopropylmalonate, lithium 2,2-dimethylmalonate, lithium 2,2-diethylmalonate, lithium 2,2-dipropylmalonate, lithium 2,2-dibutylmalonate, lithium 2,2-dipentylmalonate, lithium 2,2-dihexylmalonate, lithium 2,2-diheptylmalonate, lithium 2,2-dioctylmalonate, lithium 2,2-dinonylmalonate, lithium 2,2-didecylmalonate, lithium 2,2-diundecylmalonate, lithium 2,2-didodecylmalonate, lithium 2-dodecyl-2-undecylmalonate, lithium 2-decyl-2-dodecylmalonate, lithium 2-dodecyl-2-nonylmalonate, lithium 2-dodecyl-2-octylmalonate, lithium 2-dodecyl-2-heptylmalonate, lithium 2-dodecyl-2-hexylmalonate, lithium 2-dodecyl-2-pentylmalonate, lithium 2-butyl-2-dodecylmalonate, lithium 2-dodecyl-2-propylmalonate, lithium 2-dodecyl-2-ethylmalonate, lithium 2-dodecyl-2-methylmalonate, lithium 2-dodecylmalonate, lithium 2-undecylmalonate, lithium 2-decylmalonate, lithium 2-nonylmalonate, lithium 2-octylmalonate, lithium 2-heptylmalonate, lithium 2-hexylmalonate, lithium 2-pentylmalonate, lithium 2-butylmalonate, lithium 2-propylmalonate, lithium 2-ethylmalonate, lithium 2-methylmalonate, lithium 2-phenylmalonate, lithium 2-(p-tolyl)malonate, lithium 2-mesitylmalonate, lithium 2-(4-(tert-butyl)phenyl)malonate, lithium 2-(4-(tert-butyl)-2-methylphenyl)malonate, lithium 2-(4-(tert-butyl)-2,6-dimethylphenyl)malonate, lithium 2,2-diphenylmalonate, lithium 2-methyl-2-phenylmalonate, lithium 2-ethyl-2-phenylmalonate, lithium 2-phenyl-2-propylmalonate, lithium 2-butyl-2-phenylmalonate, lithium 2-pentyl-2-phenylmalonate, lithium 2-hexyl-2-phenylmalonate, lithium 2-heptyl-2-phenylmalonate, lithium 2-octyl-2-phenylmalonate, lithium 2-nonyl-2-phenylmalonate, lithium 2-decyl-2-phenylmalonate, lithium 2-phenyl-2-undecylmalonate, lithium 2-dodecyl-2-phenylmalonate, lithium 2-isopropyl-2-methylmalonate, lithium 2,2-diisopropylmalonate, lithium 2-isopropylmalonate, lithium 2-(tert-butyl)malonate, lithium 2-ditert-butylmalonate, lithium 2-(tert-butyl)-2-methylmalonate, lithium 2-(tert-butyl)-2-ethylmalonate, lithium 2-ethyl-2-isopropylmalonate, lithium 2-isopropyl-2-propylmalonate, lithium 2-butyl-2-isopropylmalonate, lithium 2-isopropyl-2-pentylmalonate, lithium 2-hexyl-2-isopropylmalonate, lithium 2-heptyl-2-isopropylmalonate, lithium 2-isopropyl-2-octylmalonate, lithium 2-isopropyl-2-nonylmalonate, lithium 2-decyl-2-isopropylmalonate, lithium 2-isopropyl-2-undecylmalonate, lithium 2-(tert-butyl)-2-undecylmalonate, lithium 2-(tert-butyl)-2-decylmalonate, lithium 2-(tert-butyl)-2-nonylmalonate, lithium 2-(tert-butyl)-2-octylmalonate, lithium 2-(tert-butyl)-2-heptylmalonate, lithium 2-(tert-butyl)-2-hexylmalonate, lithium 2-(tert-butyl)-2-pentylmalonate, lithium 2-(tert-butyl)-2-butylmalonate, lithium 2-(tert-butyl)-2-propylmalonate, lithium 2-(tert-butyl)-2-ethylmalonate, lithium 2-(tert-butyl)-2-phenylmalonate, lithium 2-isopropyl-2-phenylmalonate, lithium 2-(sec-butyl)malonate, lithium 2-(sec-butyl)-2-methylmalonate, lithium 2-methyl-2-(pentan-2-yl)malonate, lithium 2-(hexan-2-yl)-2-methylmalonate, lithium 2-(heptan-2-yl)-2-methylmalonate, lithium 2-methyl-2-(octan-2-yl)malonate, lithium 2-methyl-2-(nonan-2-yl)malonate, lithium 2-methyl-2-(octan-3-yl)malonate, lithium 2-(octan-3-yl)-2-octylmalonate, lithium 2-benzyl-2-methylmalonate, lithium 2,2-dibenzylmalonate, lithium 2-benzyl-2-ethylmalonate, lithium 2-benzyl-2-isopropylmalonate, lithium 2-benzyl-2-(tert-butyl)malonate, lithium 2-cyclohexylmalonate, lithium 2-cyclohexyl-2-methylmalonate, lithium 2-cyclohexyl-2-ethylmalonate, lithium 2-cyclohexyl-2-isopropylmalonate, lithium 2-(tert-butyl)-2-cyclohexylmalonate, lithium 2,2-dicyclohexylmalonate, lithium 2-cyclohexyl-2-(pentan-3-yl)malonate, lithium 2-ethylmalonate, lithium 2-isopropylmalonate, lithium 2-(tert-butyl)malonate, lithium 2-propylmalonate, lithium 2-butylmalonate, lithium 2-pentylmalonate, lithium 2-(2-methylpentyl)malonate, lithium 2-(2-ethylpentyl)malonate, lithium 2-(3-ethylhexan-2-yl)malonate, lithium 2-hexylmalonate, lithium 2-heptylmalonate, lithium 2-octylmalonate, lithium 2-nonylmalonate, lithium 2-decylmalonate, lithium 2-decyl-2-isopropylmalonate, potassium 2,2-dimethylmalonate, potassium 2,2-diethylmalonate, potassium 2,2-dipropylmalonate, potassium 2,2-dibutylmalonate, potassium 2,2-dipentylmalonate, potassium 2,2-dihexylmalonate, potassium 2,2-diheptylmalonate, potassium 2,2-dioctylmalonate, potassium 2,2-dinonylmalonate, potassium 2,2-didecylmalonate, potassium 2,2-diundecylmalonate, potassium 2,2-didodecylmalonate, potassium 2-dodecyl-2-undecylmalonate, potassium 2-decyl-2-dodecylmalonate, potassium 2-dodecyl-2-nonylmalonate, potassium 2-dodecyl-2-octylmalonate, potassium 2-dodecyl-2-heptylmalonate, potassium 2-dodecyl-2-hexylmalonate, potassium 2-dodecyl-2-pentylmalonate, potassium 2-butyl-2-dodecylmalonate, potassium 2-dodecyl-2-propylmalonate, potassium 2-dodecyl-2-ethylmalonate, potassium 2-dodecyl-2-methylmalonate, potassium 2-dodecylmalonate, potassium 2-undecylmalonate, potassium 2-decylmalonate, potassium 2-nonylmalonate, potassium 2-octylmalonate, potassium 2-heptylmalonate, potassium 2-hexylmalonate, potassium 2-pentylmalonate, potassium 2-butylmalonate, potassium 2-propylmalonate, potassium 2-ethylmalonate, potassium 2-methylmalonate, potassium 2-phenylmalonate, potassium 2-(p-tolyl)malonate, potassium 2-mesitylmalonate, potassium 2-(4-(tert-butyl)phenyl)malonate, potassium 2-(4-(tert-butyl)-2-methylphenyl)malonate, potassium 2-(4-(tert-butyl)-2,6-dimethylphenyl)malonate, potassium 2,2-diphenylmalonate, potassium 2-methyl-2-phenylmalonate, potassium 2-ethyl-2-phenylmalonate, potassium 2-phenyl-2-propylmalonate, potassium 2-butyl-2-phenylmalonate, potassium 2-pentyl-2-phenylmalonate, potassium 2-hexyl-2-phenylmalonate, potassium 2-heptyl-2-phenylmalonate, potassium 2-octyl-2-phenylmalonate, potassium 2-nonyl-2-phenylmalonate, potassium 2-decyl-2-phenylmalonate, potassium 2-phenyl-2-undecylmalonate, potassium 2-dodecyl-2-phenylmalonate, potassium 2-isopropyl-2-methylmalonate, potassium 2,2-diisopropylmalonate, potassium 2-isopropylmalonate, potassium 2-(tert-butyl)malonate, potassium 2-ditert-butylmalonate, potassium 2-(tert-butyl)-2-methylmalonate, potassium 2-(tert-butyl)-2-ethylmalonate, potassium 2-ethyl-2-isopropylmalonate, potassium 2-isopropyl-2-propylmalonate, potassium 2-butyl-2-isopropylmalonate, potassium 2-isopropyl-2-pentylmalonate, potassium 2-hexyl-2-isopropylmalonate, potassium 2-heptyl-2-isopropylmalonate, potassium 2-isopropyl-2-octylmalonate, potassium 2-isopropyl-2-nonylmalonate, potassium 2-decyl-2-isopropylmalonate, potassium 2-isopropyl-2-undecylmalonate, potassium 2-(tert-butyl)-2-undecylmalonate, potassium 2-(tert-butyl)-2-decylmalonate, potassium 2-(tert-butyl)-2-nonylmalonate, potassium 2-(tert-butyl)-2-octylmalonate, potassium 2-(tert-butyl)-2-heptylmalonate, potassium 2-(tert-butyl)-2-hexylmalonate, potassium 2-(tert-butyl)-2-pentylmalonate, potassium 2-(tert-butyl)-2-butylmalonate, potassium 2-(tert-butyl)-2-propylmalonate, potassium 2-(tert-butyl)-2-ethylmalonate, potassium 2-(tert-butyl)-2-phenylmalonate, potassium 2-isopropyl-2-phenylmalonate, potassium 2-(sec-butyl)malonate, potassium 2-(sec-butyl)-2-methylmalonate, potassium 2-methyl-2-(pentan-2-yl)malonate, potassium 2-(hexan-2-yl)-2-methylmalonate, potassium 2-(heptan-2-yl)-2-methylmalonate, potassium 2-methyl-2-(octan-2-yl)malonate, potassium 2-methyl-2-(nonan-2-yl)malonate, potassium 2-methyl-2-(octan-3-yl)malonate, potassium 2-(octan-3-yl)-2-octylmalonate, potassium 2-benzyl-2-methyl malonate, potassium 2,2-dibenzylmalonate, potassium 2-benzyl-2-ethylmalonate, potassium 2-benzyl-2-isopropylmalonate, potassium 2-benzyl-2-(tert-butyl)malonate, potassium 2-cyclohexylmalonate, potassium 2-cyclohexyl-2-methylmalonate, potassium 2-cyclohexyl-2-ethylmalonate, potassium 2-cyclohexyl-2-isopropylmalonate, potassium 2-(tert-butyl)-2-cyclohexylmalonate, potassium 2,2-dicyclohexylmalonate, potassium 2-cyclohexyl-2-(pentan-3-yl)malonate, potassium 2-ethylmalonate, potassium 2-isopropylmalonate, potassium 2-(tert-butyl)malonate, potassium 2-propylmalonate, potassium 2-butylmalonate, potassium 2-pentylmalonate, potassium 2-(2-methylpentyl)malonate, potassium 2-(2-ethylpentyl)malonate, potassium 2-(3-ethylhexan-2-yl)malonate, potassium 2-hexylmalonate, potassium 2-heptylmalonate, potassium 2-octylmalonate, potassium 2-nonylmalonate, potassium 2-decylmalonate, potassium 2-decyl-2-isopropylmalonate, barium 2,2-dimethylmalonate, barium 2,2-diethylmalonate, barium 2,2-dipropylmalonate, barium 2,2-dibutylmalonate, barium 2,2-dipentylmalonate, barium 2,2-dihexylmalonate, barium 2,2-diheptylmalonate, barium 2,2-dioctylmalonate, barium 2,2-dinonylmalonate, barium 2,2-didecylmalonate, barium 2,2-diundecylmalonate, barium 2,2-didodecylmalonate, barium 2-dodecyl-2-undecylmalonate, barium 2-decyl-2-dodecylmalonate, barium 2-dodecyl-2-nonylmalonate, barium 2-dodecyl-2-octylmalonate, barium 2-dodecyl-2-heptylmalonate, barium 2-dodecyl-2-hexylmalonate, barium 2-dodecyl-2-pentylmalonate, barium 2-butyl-2-dodecylmalonate, barium 2-dodecyl-2-propylmalonate, barium 2-dodecyl-2-ethylmalonate, barium 2-dodecyl-2-methylmalonate, barium 2-dodecylmalonate, barium 2-undecylmalonate, barium 2-decylmalonate, barium 2-nonylmalonate, barium 2-octylmalonate, barium 2-heptylmalonate, barium 2-hexylmalonate, barium 2-pentylmalonate, barium 2-butylmalonate, barium 2-propylmalonate, barium 2-ethylmalonate, barium 2-methylmalonate, barium 2-phenylmalonate, barium 2-(p-tolyl)malonate, barium 2-mesitylmalonate, barium 2-(4-(tert-butyl)phenyl)malonate, barium 2-(4-(tert-butyl)-2-methylphenyl)malonate, barium 2-(4-(tert-butyl)-2,6-dimethyl phenyl)malonate, barium 2,2-diphenylmalonate, barium 2-methyl-2-phenylmalonate, barium 2-ethyl-2-phenylmalonate, barium 2-phenyl-2-propylmalonate, barium 2-butyl-2-phenylmalonate, barium 2-pentyl-2-phenylmalonate, barium 2-hexyl-2-phenylmalonate, barium 2-heptyl-2-phenylmalonate, barium 2-octyl-2-phenylmalonate, barium 2-nonyl-2-phenylmalonate, barium 2-decyl-2-phenylmalonate, barium 2-phenyl-2-undecylmalonate, barium 2-dodecyl-2-phenylmalonate, barium 2-isopropyl-2-methylmalonate, barium 2,2-diisopropylmalonate, barium 2-isopropylmalonate, barium 2-(tert-butyl)malonate, barium 2-ditert-butylmalonate, barium 2-(tert-butyl)-2-methylmalonate, barium 2-(tert-butyl)-2-ethylmalonate, barium 2-ethyl-2-isopropylmalonate, barium 2-isopropyl-2-propylmalonate, barium 2-butyl-2-isopropylmalonate, barium 2-isopropyl-2-pentylmalonate, barium 2-hexyl-2-isopropylmalonate, barium 2-heptyl-2-isopropylmalonate, barium 2-isopropyl-2-octylmalonate, barium 2-isopropyl-2-nonylmalonate, barium 2-decyl-2-isopropylmalonate, barium 2-isopropyl-2-undecylmalonate, barium 2-(tert-butyl)-2-undecylmalonate, barium 2-(tert-butyl)-2-decylmalonate, barium 2-(tert-butyl)-2-nonylmalonate, barium 2-(tert-butyl)-2-octylmalonate, barium 2-(tert-butyl)-2-heptylmalonate, barium 2-(tert-butyl)-2-hexylmalonate, barium 2-(tert-butyl)-2-pentylmalonate, barium 2-(tert-butyl)-2-butylmalonate, barium 2-(tert-butyl)-2-propylmalonate, barium 2-(tert-butyl)-2-ethylmalonate, barium 2-(tert-butyl)-2-phenylmalonate, barium 2-isopropyl-2-phenylmalonate, barium 2-(sec-butyl)malonate, barium 2-(sec-butyl)-2-methylmalonate, barium 2-methyl-2-(pentan-2-yl)malonate, barium 2-(hexan-2-yl)-2-methylmalonate, barium 2-(heptan-2-yl)-2-methylmalonate, barium 2-methyl-2-(octan-2-yl)malonate, barium 2-methyl-2-(nonan-2-yl)malonate, barium 2-methyl-2-(octan-3-yl)malonate, barium 2-(octan-3-yl)-2-octylmalonate, barium 2-benzyl-2-methylmalonate, barium 2,2-dibenzylmalonate, barium 2-benzyl-2-ethylmalonate, barium 2-benzyl-2-isopropylmalonate, barium 2-benzyl-2-(tert-butyl)malonate, barium 2-cyclohexylmalonate, barium 2-cyclohexyl-2-methylmalonate, barium 2-cyclohexyl-2-ethylmalonate, barium 2-cyclohexyl-2-isopropylmalonate, barium 2-(tert-butyl)-2-cyclohexylmalonate, barium 2,2-dicyclohexylmalonate, barium 2-cyclohexyl-2-(pentan-3-yl)malonate, barium 2-ethylmalonate, barium 2-isopropylmalonate, barium 2-(tert-butyl)malonate, barium 2-propylmalonate, barium 2-butylmalonate, barium 2-pentylmalonate, barium 2-(2-methylpentyl)malonate, barium 2-(2-ethylpentyl)malonate, barium 2-(3-ethylhexan-2-yl)malonate, barium 2-hexylmalonate, barium 2-heptylmalonate, barium 2-octylmalonate, barium 2-nonylmalonate, barium 2-decylmalonate, barium 2-decyl-2-isopropylmalonate, calcium 2,2-dimethylmalonate, calcium 2,2-diethylmalonate, calcium 2,2-dipropylmalonate, calcium 2,2-dibutylmalonate, calcium 2,2-dipentylmalonate, calcium 2,2-dihexylmalonate, calcium 2,2-diheptylmalonate, calcium 2,2-dioctylmalonate, calcium 2,2-dinonylmalonate, calcium 2,2-didecylmalonate, calcium 2,2-diundecylmalonate, calcium 2,2-didodecylmalonate, calcium 2-dodecyl-2-undecylmalonate, calcium 2-decyl-2-dodecylmalonate, calcium 2-dodecyl-2-nonylmalonate, calcium 2-dodecyl-2-octylmalonate, calcium 2-dodecyl-2-heptylmalonate, calcium 2-dodecyl-2-hexylmalonate, calcium 2-dodecyl-2-pentylmalonate, calcium 2-butyl-2-dodecylmalonate, calcium 2-dodecyl-2-propylmalonate, calcium 2-dodecyl-2-ethylmalonate, calcium 2-dodecyl-2-methylmalonate, calcium 2-dodecylmalonate, calcium 2-undecylmalonate, calcium 2-decylmalonate, calcium 2-nonylmalonate, calcium 2-octylmalonate, calcium 2-heptylmalonate, calcium 2-hexylmalonate, calcium 2-pentylmalonate, calcium 2-butylmalonate, calcium 2-propylmalonate, calcium 2-ethylmalonate, calcium 2-methylmalonate, calcium 2-phenylmalonate, calcium 2-(p-tolyl)malonate, calcium 2-mesitylmalonate, calcium 2-(4-(tert-butyl)phenyl)malonate, calcium 2-(4-(tert-butyl)-2-methylphenyl)malonate, calcium 2-(4-(tert-butyl)-2,6-dimethylphenyl)malonate, calcium 2,2-diphenylmalonate, calcium 2-methyl-2-phenylmalonate, calcium 2-ethyl-2-phenylmalonate, calcium 2-phenyl-2-propylmalonate, calcium 2-butyl-2-phenylmalonate, calcium 2-pentyl-2-phenylmalonate, calcium 2-hexyl-2-phenylmalonate, calcium 2-heptyl-2-phenylmalonate, calcium 2-octyl-2-phenylmalonate, calcium 2-nonyl-2-phenylmalonate, calcium 2-decyl-2-phenylmalonate, calcium 2-phenyl-2-undecylmalonate, calcium 2-dodecyl-2-phenylmalonate, calcium 2-isopropyl-2-methylmalonate, calcium 2,2-diisopropylmalonate, calcium 2-isopropylmalonate, calcium 2-(tert-butyl)malonate, calcium 2-ditert-butylmalonate, calcium 2-(tert-butyl)-2-methylmalonate, calcium 2-(tert-butyl)-2-ethylmalonate, calcium 2-ethyl-2-isopropylmalonate, calcium 2-isopropyl-2-propylmalonate, calcium 2-butyl-2-isopropylmalonate, calcium 2-isopropyl-2-pentylmalonate, calcium 2-hexyl-2-isopropylmalonate, calcium 2-heptyl-2-isopropylmalonate, calcium 2-isopropyl-2-octylmalonate, calcium 2-isopropyl-2-nonylmalonate, calcium 2-decyl-2-isopropylmalonate, calcium 2-isopropyl-2-undecylmalonate, calcium 2-(tert-butyl)-2-undecylmalonate, calcium 2-(tert-butyl)-2-decylmalonate, calcium 2-(tert-butyl)-2-nonylmalonate, calcium 2-(tert-butyl)-2-octylmalonate, calcium 2-(tert-butyl)-2-heptylmalonate, calcium 2-(tert-butyl)-2-hexylmalonate, calcium 2-(tert-butyl)-2-pentylmalonate, calcium 2-(tert-butyl)-2-butylmalonate, calcium 2-(tert-butyl)-2-propylmalonate, calcium 2-(tert-butyl)-2-ethylmalonate, calcium 2-(tert-butyl)-2-phenylmalonate, calcium 2-isopropyl-2-phenylmalonate, calcium 2-(sec-butyl)malonate, calcium 2-(sec-butyl)-2-methylmalonate, calcium 2-methyl-2-(pentan-2-yl)malonate, calcium 2-(hexan-2-yl)-2-methylmalonate, calcium 2-(heptan-2-yl)-2-methylmalonate, calcium 2-methyl-2-(octan-2-yl)malonate, calcium 2-methyl-2-(nonan-2-yl)malonate, calcium 2-methyl-2-(octan-3-yl)malonate, calcium 2-(octan-3-yl)-2-octylmalonate, calcium 2-benzyl-2-methylmalonate, calcium 2,2-dibenzylmalonate, calcium 2-benzyl-2-ethylmalonate, calcium 2-benzyl-2-isopropylmalonate, calcium 2-benzyl-2-(tert-butyl)malonate, calcium 2-cyclohexylmalonate, calcium 2-cyclohexyl-2-methylmalonate, calcium 2-cyclohexyl-2-ethylmalonate, calcium 2-cyclohexyl-2-isopropylmalonate, calcium 2-(tert-butyl)-2-cyclohexylmalonate, calcium 2,2-dicyclohexylmalonate, calcium 2-cyclohexyl-2-(pentan-3-yl)malonate, calcium 2-ethylmalonate, calcium 2-isopropylmalonate, calcium 2-(tert-butyl)malonate, calcium 2-propylmalonate, calcium 2-butylmalonate, calcium 2-pentylmalonate, calcium 2-(2-methylpentyl)malonate, calcium 2-(2-ethylpentyl)malonate, calcium 2-(3-ethylhexan-2-yl)malonate, calcium 2-hexylmalonate, calcium 2-heptylmalonate, calcium 2-octylmalonate, calcium 2-nonylmalonate, calcium 2-decylmalonate, calcium 2-decyl-2-isopropylmalonate, potassium sodium 2,2-dimethylmalonate, potassium sodium 2,2-diethylmalonate, potassium sodium 2,2-dipropylmalonate, potassium sodium 2,2-dibutylmalonate, potassium sodium 2,2-dipentylmalonate, potassium sodium 2,2-dihexylmalonate, potassium sodium 2,2-diheptylmalonate, potassium sodium 2,2-dioctylmalonate, potassium sodium 2,2-dinonylmalonate, potassium sodium 2,2-didecylmalonate, potassium sodium 2,2-diundecylmalonate, potassium sodium 2,2-didodecylmalonate, potassium sodium 2-dodecyl-2-undecylmalonate, potassium sodium 2-decyl-2-dodecylmalonate, potassium sodium 2-dodecyl-2-nonylmalonate, potassium sodium 2-dodecyl-2-octylmalonate, potassium sodium 2-dodecyl-2-heptylmalonate, potassium sodium 2-dodecyl-2-hexylmalonate, potassium sodium 2-dodecyl-2-pentylmalonate, potassium sodium 2-butyl-2-dodecylmalonate, potassium sodium 2-dodecyl-2-propylmalonate, potassium sodium 2-dodecyl-2-ethylmalonate, potassium sodium 2-dodecyl-2-methylmalonate, potassium sodium 2-dodecylmalonate, potassium sodium 2-undecylmalonate, potassium sodium 2-decylmalonate, potassium sodium 2-nonylmalonate, potassium sodium 2-octylmalonate, potassium sodium 2-heptylmalonate, potassium sodium 2-hexylmalonate, potassium sodium 2-pentylmalonate, potassium sodium 2-butylmalonate, potassium sodium 2-propylmalonate, potassium sodium 2-ethylmalonate, potassium sodium 2-methylmalonate, potassium sodium 2-phenylmalonate, potassium sodium 2-(p-tolyl)malonate, potassium sodium 2-mesitylmalonate, potassium sodium 2-(4-(tert-butyl)phenyl)malonate, potassium sodium 2-(4-(tert-butyl)-2-methylphenyl)malonate, potassium sodium 2-(4-(tert-butyl)-2,6-dimethylphenyl)malonate, potassium sodium 2,2-diphenylmalonate, potassium sodium 2-methyl-2-phenylmalonate, potassium sodium 2-ethyl-2-phenylmalonate, potassium sodium 2-phenyl-2-propylmalonate, potassium sodium 2-butyl-2-phenylmalonate, potassium sodium 2-pentyl-2-phenylmalonate, potassium sodium 2-hexyl-2-phenylmalonate, potassium sodium 2-heptyl-2-phenylmalonate, potassium sodium 2-octyl-2-phenylmalonate, potassium sodium 2-nonyl-2-phenylmalonate, potassium sodium 2-decyl-2-phenylmalonate, potassium sodium 2-phenyl-2-undecylmalonate, potassium sodium 2-dodecyl-2-phenylmalonate, potassium sodium 2-isopropyl-2-methylmalonate, potassium sodium 2,2-diisopropylmalonate, potassium sodium 2-isopropylmalonate, potassium sodium 2-(tert-butyl)malonate, potassium sodium 2-ditert-butylmalonate, potassium sodium 2-(tert-butyl)-2-methylmalonate, potassium sodium 2-(tert-butyl)-2-ethylmalonate, potassium sodium 2-ethyl-2-isopropylmalonate, potassium sodium 2-isopropyl-2-propylmalonate, potassium sodium 2-butyl-2-isopropylmalonate, potassium sodium 2-isopropyl-2-pentylmalonate, potassium sodium 2-hexyl-2-isopropylmalonate, potassium sodium 2-heptyl-2-isopropylmalonate, potassium sodium 2-isopropyl-2-octylmalonate, potassium sodium 2-isopropyl-2-nonylmalonate, potassium sodium 2-decyl-2-isopropylmalonate, potassium sodium 2-isopropyl-2-undecylmalonate, potassium sodium 2-(tert-butyl)-2-undecylmalonate, potassium sodium 2-(tert-butyl)-2-decylmalonate, potassium sodium 2-(tert-butyl)-2-nonylmalonate, potassium sodium 2-(tert-butyl)-2-octylmalonate, potassium sodium 2-(tert-butyl)-2-heptylmalonate, potassium sodium 2-(tert-butyl)-2-hexylmalonate, potassium sodium 2-(tert-butyl)-2-pentylmalonate, potassium sodium 2-(tert-butyl)-2-butylmalonate, potassium sodium 2-(tert-butyl)-2-propylmalonate, potassium sodium 2-(tert-butyl)-2-ethylmalonate, potassium sodium 2-(tert-butyl)-2-phenylmalonate, potassium sodium 2-isopropyl-2-phenylmalonate, potassium sodium 2-(sec-butyl)malonate, potassium sodium 2-(sec-butyl)-2-methylmalonate, potassium sodium 2-methyl-2-(pentan-2-yl)malonate, potassium sodium 2-(hexan-2-yl)-2-methylmalonate, potassium sodium 2-(heptan-2-yl)-2-methylmalonate, potassium sodium 2-methyl-2-(octan-2-yl)malonate, potassium sodium 2-methyl-2-(nonan-2-yl)malonate, potassium sodium 2-methyl-2-(octan-3-yl)malonate, potassium sodium 2-(octan-3-yl)-2-octylmalonate, potassium sodium 2-benzyl-2-methylmalonate, potassium sodium 2,2-dibenzylmalonate, potassium sodium 2-benzyl-2-ethylmalonate, potassium sodium 2-benzyl-2-isopropylmalonate, potassium sodium 2-benzyl-2-(tert-butyl)malonate, potassium sodium 2-cyclohexylmalonate, potassium sodium 2-cyclohexyl-2-methylmalonate, potassium sodium 2-cyclohexyl-2-ethylmalonate, potassium sodium 2-cyclohexyl-2-isopropylmalonate, potassium sodium 2-(tert-butyl)-2-cyclohexylmalonate, potassium sodium 2,2-dicyclohexylmalonate, potassium sodium 2-cyclohexyl-2-(pentan-3-yl)malonate, potassium sodium 2-ethylmalonate, potassium sodium 2-isopropylmalonate, potassium sodium 2-(tert-butyl)malonate, potassium sodium 2-propylmalonate, potassium sodium 2-butylmalonate, potassium sodium 2-pentylmalonate, potassium sodium 2-(2-methylpentyl)malonate, potassium sodium 2-(2-ethylpentyl)malonate, potassium sodium 2-(3-ethylhexan-2-yl)malonate, potassium sodium 2-hexylmalonate, potassium sodium 2-heptylmalonate, potassium sodium 2-octylmalonate, potassium sodium 2-nonylmalonate, potassium sodium 2-decylmalonate, potassium sodium 2-decyl-2-isopropylmalonate, lithium sodium 2,2-dimethylmalonate, lithium sodium 2,2-diethylmalonate, lithium sodium 2,2-dipropylmalonate, lithium sodium 2,2-dibutylmalonate, lithium sodium 2,2-dipentylmalonate, lithium sodium 2,2-dihexylmalonate, lithium sodium 2,2-diheptylmalonate, lithium sodium 2,2-dioctylmalonate, lithium sodium 2,2-dinonylmalonate, lithium sodium 2,2-didecylmalonate, lithium sodium 2,2-diundecylmalonate, lithium sodium 2,2-didodecylmalonate, lithium sodium 2-dodecyl-2-undecylmalonate, lithium sodium 2-decyl-2-dodecylmalonate, lithium sodium 2-dodecyl-2-nonylmalonate, lithium sodium 2-dodecyl-2-octylmalonate, lithium sodium 2-dodecyl-2-heptylmalonate, lithium sodium 2-dodecyl-2-hexylmalonate, lithium sodium 2-dodecyl-2-pentylmalonate, lithium sodium 2-butyl-2-dodecylmalonate, lithium sodium 2-dodecyl-2-propylmalonate, lithium sodium 2-dodecyl-2-ethylmalonate, lithium sodium 2-dodecyl-2-methylmalonate, lithium sodium 2-dodecylmalonate, lithium sodium 2-undecylmalonate, lithium sodium 2-decylmalonate, lithium sodium 2-nonylmalonate, lithium sodium 2-octylmalonate, lithium sodium 2-heptylmalonate, lithium sodium 2-hexylmalonate, lithium sodium 2-pentylmalonate, lithium sodium 2-butylmalonate, lithium sodium 2-propylmalonate, lithium sodium 2-ethylmalonate, lithium sodium 2-methylmalonate, lithium sodium 2-phenylmalonate, lithium sodium 2-(p-tolyl)malonate, lithium sodium 2-mesitylmalonate, lithium sodium 2-(4-(tert-butyl)phenyl)malonate, lithium sodium 2-(4-(tert-butyl)-2-methylphenyl)malonate, lithium sodium 2-(4-(tert-butyl)-2,6-dimethylphenyl)malonate, lithium sodium 2,2-diphenylmalonate, lithium sodium 2-methyl-2-phenylmalonate, lithium sodium 2-ethyl-2-phenylmalonate, lithium sodium 2-phenyl-2-propylmalonate, lithium sodium 2-butyl-2-phenylmalonate, lithium sodium 2-pentyl-2-phenylmalonate, lithium sodium 2-hexyl-2-phenylmalonate, lithium sodium 2-heptyl-2-phenylmalonate, lithium sodium 2-octyl-2-phenylmalonate, lithium sodium 2-nonyl-2-phenylmalonate, lithium sodium 2-decyl-2-phenylmalonate, lithium sodium 2-phenyl-2-undecylmalonate, lithium sodium 2-dodecyl-2-phenylmalonate, lithium sodium 2-isopropyl-2-methylmalonate, lithium sodium 2,2-diisopropylmalonate, lithium sodium 2-isopropylmalonate, lithium sodium 2-(tert-butyl)malonate, lithium sodium 2-ditert-butylmalonate, lithium sodium 2-(tert-butyl)-2-methylmalonate, lithium sodium 2-(tert-butyl)-2-ethylmalonate, lithium sodium 2-ethyl-2-isopropylmalonate, lithium sodium 2-isopropyl-2-propylmalonate, lithium sodium 2-butyl-2-isopropylmalonate, lithium sodium 2-isopropyl-2-pentylmalonate, lithium sodium 2-hexyl-2-isopropylmalonate, lithium sodium 2-heptyl-2-isopropylmalonate, lithium sodium 2-isopropyl-2-octylmalonate, lithium sodium 2-isopropyl-2-nonylmalonate, lithium sodium 2-decyl-2-isopropylmalonate, lithium sodium 2-isopropyl-2-undecylmalonate, lithium sodium 2-(tert-butyl)-2-undecylmalonate, lithium sodium 2-(tert-butyl)-2-decylmalonate, lithium sodium 2-(tert-butyl)-2-nonylmalonate, lithium sodium 2-(tert-butyl)-2-octylmalonate, lithium sodium 2-(tert-butyl)-2-heptylmalonate, lithium sodium 2-(tert-butyl)-2-hexylmalonate, lithium sodium 2-(tert-butyl)-2-pentylmalonate, lithium sodium 2-(tert-butyl)-2-butylmalonate, lithium sodium 2-(tert-butyl)-2-propylmalonate, lithium sodium 2-(tert-butyl)-2-ethylmalonate, lithium sodium 2-(tert-butyl)-2-phenylmalonate, lithium sodium 2-isopropyl-2-phenylmalonate, lithium sodium 2-(sec-butyl)malonate, lithium sodium 2-(sec-butyl)-2-methylmalonate, lithium sodium 2-methyl-2-(pentan-2-yl)malonate, lithium sodium 2-(hexan-2-yl)-2-methylmalonate, lithium sodium 2-(heptan-2-yl)-2-methylmalonate, lithium sodium 2-methyl-2-(octan-2-yl)malonate, lithium sodium 2-methyl-2-(nonan-2-yl)malonate, lithium sodium 2-methyl-2-(octan-3-yl)malonate, lithium sodium 2-(octan-3-yl)-2-octylmalonate, lithium sodium 2-benzyl-2-methylmalonate, lithium sodium 2,2-dibenzylmalonate, lithium sodium 2-benzyl-2-ethylmalonate, lithium sodium 2-benzyl-2-isopropylmalonate, lithium sodium 2-benzyl-2-(tert-butyl)malonate, lithium sodium 2-cyclohexylmalonate, lithium sodium 2-cyclohexyl-2-methylmalonate, lithium sodium 2-cyclohexyl-2-ethylmalonate, lithium sodium 2-cyclohexyl-2-isopropylmalonate, lithium sodium 2-(tert-butyl)-2-cyclohexylmalonate, lithium sodium 2,2-dicyclohexylmalonate, lithium sodium 2-cyclohexyl-2-(pentan-3-yl)malonate, lithium sodium 2-ethylmalonate, lithium sodium 2-isopropylmalonate, lithium sodium 2-(tert-butyl)malonate, lithium sodium 2-propylmalonate, lithium sodium 2-butylmalonate, lithium sodium 2-pentylmalonate, lithium sodium 2-(2-methylpentyl)malonate, lithium sodium 2-(2-ethylpentyl)malonate, lithium sodium 2-(3-ethylhexan-2-yl)malonate, lithium sodium 2-hexylmalonate, lithium sodium 2-heptylmalonate, lithium sodium 2-octylmalonate, lithium sodium 2-nonylmalonate, lithium sodium 2-decylmalonate, lithium sodium 2-decyl-2-isopropylmalonate, lithium potassium 2,2-dimethylmalonate, lithium potassium 2,2-diethylmalonate, lithium potassium 2,2-dipropylmalonate, lithium potassium 2,2-dibutylmalonate, lithium potassium 2,2-dipentylmalonate, lithium potassium 2,2-dihexylmalonate, lithium potassium 2,2-diheptylmalonate, lithium potassium 2,2-dioctylmalonate, lithium potassium 2,2-dinonylmalonate, lithium potassium 2,2-didecylmalonate, lithium potassium 2,2-diundecylmalonate, lithium potassium 2,2-didodecylmalonate, lithium potassium 2-dodecyl-2-undecylmalonate, lithium potassium 2-decyl-2-dodecylmalonate, lithium potassium 2-dodecyl-2-nonylmalonate, lithium potassium 2-dodecyl-2-octylmalonate, lithium potassium 2-dodecyl-2-heptylmalonate, lithium potassium 2-dodecyl-2-hexylmalonate, lithium potassium 2-dodecyl-2-pentylmalonate, lithium potassium 2-butyl-2-dodecylmalonate, lithium potassium 2-dodecyl-2-propylmalonate, lithium potassium 2-dodecyl-2-ethylmalonate, lithium potassium 2-dodecyl-2-methylmalonate, lithium potassium 2-dodecylmalonate, lithium potassium 2-undecylmalonate, lithium potassium 2-decylmalonate, lithium potassium 2-nonylmalonate, lithium potassium 2-octylmalonate, lithium potassium 2-heptylmalonate, lithium potassium 2-hexylmalonate, lithium potassium 2-pentylmalonate, lithium potassium 2-butylmalonate, lithium potassium 2-propylmalonate, lithium potassium 2-ethylmalonate, lithium potassium 2-methylmalonate, lithium potassium 2-phenylmalonate, lithium potassium 2-(p-tolyl)malonate, lithium potassium 2-mesitylmalonate, lithium potassium 2-(4-(tert-butyl)phenyl)malonate, lithium potassium 2-(4-(tert-butyl)-2-methylphenyl)malonate, lithium potassium 2-(4-(tert-butyl)-2,6-dimethylphenyl)malonate, lithium potassium 2,2-diphenylmalonate, lithium potassium 2-methyl-2-phenylmalonate, lithium potassium 2-ethyl-2-phenylmalonate, lithium potassium 2-phenyl-2-propylmalonate, lithium potassium 2-butyl-2-phenylmalonate, lithium potassium 2-pentyl-2-phenylmalonate, lithium potassium 2-hexyl-2-phenylmalonate, lithium potassium 2-heptyl-2-phenylmalonate, lithium potassium 2-octyl-2-phenylmalonate, lithium potassium 2-nonyl-2-phenylmalonate, lithium potassium 2-decyl-2-phenylmalonate, lithium potassium 2-phenyl-2-undecylmalonate, lithium potassium 2-dodecyl-2-phenylmalonate, lithium potassium 2-isopropyl-2-methylmalonate, lithium potassium 2,2-diisopropylmalonate, lithium potassium 2-isopropylmalonate, lithium potassium 2-(tert-butyl)malonate, lithium potassium 2-ditert-butylmalonate, lithium potassium 2-(tert-butyl)-2-methylmalonate, lithium potassium 2-(tert-butyl)-2-ethylmalonate, lithium potassium 2-ethyl-2-isopropylmalonate, lithium potassium 2-isopropyl-2-propylmalonate, lithium potassium 2-butyl-2-isopropylmalonate, lithium potassium 2-isopropyl-2-pentylmalonate, lithium potassium 2-hexyl-2-isopropylmalonate, lithium potassium 2-heptyl-2-isopropylmalonate, lithium potassium 2-isopropyl-2-octylmalonate, lithium potassium 2-isopropyl-2-nonylmalonate, lithium potassium 2-decyl-2-isopropylmalonate, lithium potassium 2-isopropyl-2-undecylmalonate, lithium potassium 2-(tert-butyl)-2-undecylmalonate, lithium potassium 2-(tert-butyl)-2-decylmalonate, lithium potassium 2-(tert-butyl)-2-nonylmalonate, lithium potassium 2-(tert-butyl)-2-octylmalonate, lithium potassium 2-(tert-butyl)-2-heptylmalonate, lithium potassium 2-(tert-butyl)-2-hexylmalonate, lithium potassium 2-(tert-butyl)-2-pentylmalonate, lithium potassium 2-(tert-butyl)-2-butylmalonate, lithium potassium 2-(tert-butyl)-2-propylmalonate, lithium potassium 2-(tert-butyl)-2-ethylmalonate, lithium potassium 2-(tert-butyl)-2-phenylmalonate, lithium potassium 2-isopropyl-2-phenylmalonate, lithium potassium 2-(sec-butyl)malonate, lithium potassium 2-(sec-butyl)-2-methylmalonate, lithium potassium 2-methyl-2-(pentan-2-yl)malonate, lithium potassium 2-(hexan-2-yl)-2-methylmalonate, lithium potassium 2-(heptan-2-yl)-2-methylmalonate, lithium potassium 2-methyl-2-(octan-2-yl)malonate, lithium potassium 2-methyl-2-(nonan-2-yl)malonate, lithium potassium 2-methyl-2-(octan-3-yl)malonate, lithium potassium 2-(octan-3-yl)-2-octylmalonate, lithium potassium 2-benzyl-2-methylmalonate, lithium potassium 2,2-dibenzylmalonate, lithium potassium 2-benzyl-2-ethylmalonate, lithium potassium 2-benzyl-2-isopropylmalonate, lithium potassium 2-benzyl-2-(tert-butyl)malonate, lithium potassium 2-cyclohexylmalonate, lithium potassium 2-cyclohexyl-2-methylmalonate, lithium potassium 2-cyclohexyl-2-ethylmalonate, lithium potassium 2-cyclohexyl-2-isopropylmalonate, lithium potassium 2-(tert-butyl)-2-cyclohexylmalonate, lithium potassium 2,2-dicyclohexylmalonate, lithium potassium 2-cyclohexyl-2-(pentan-3-yl)malonate, lithium potassium 2-ethylmalonate, lithium potassium 2-isopropylmalonate, lithium potassium 2-(tert-butyl)malonate, lithium potassium 2-propylmalonate, lithium potassium 2-butylmalonate, lithium potassium 2-pentylmalonate, lithium potassium 2-(2-methylpentyl)malonate, lithium potassium 2-(2-ethylpentyl)malonate, lithium potassium 2-(3-ethylhexan-2-yl)malonate, lithium potassium 2-hexylmalonate, lithium potassium 2-heptylmalonate, lithium potassium 2-octylmalonate, lithium potassium 2-nonylmalonate, lithium potassium 2-decylmalonate, lithium potassium 2-decyl-2-isopropylmalonate, magnesium 2,2-dimethylmalonate, magnesium 2,2-diethylmalonate, magnesium 2,2-dipropylmalonate, magnesium 2,2-dibutylmalonate, magnesium 2,2-dipentylmalonate, magnesium 2,2-dihexylmalonate, magnesium 2,2-diheptylmalonate, magnesium 2,2-dioctylmalonate, magnesium 2,2-dinonylmalonate, magnesium 2,2-didecylmalonate, magnesium 2,2-diundecylmalonate, magnesium 2,2-didodecylmalonate, magnesium 2-dodecyl-2-undecylmalonate, magnesium 2-decyl-2-dodecylmalonate, magnesium 2-dodecyl-2-nonylmalonate, magnesium 2-dodecyl-2-octylmalonate, magnesium 2-dodecyl-2-heptylmalonate, magnesium 2-dodecyl-2-hexylmalonate, magnesium 2-dodecyl-2-pentylmalonate, magnesium 2-butyl-2-dodecylmalonate, magnesium 2-dodecyl-2-propylmalonate, magnesium 2-dodecyl-2-ethylmalonate, magnesium 2-dodecyl-2-methylmalonate, magnesium 2-dodecylmalonate, magnesium 2-undecylmalonate, magnesium 2-decylmalonate, magnesium 2-nonylmalonate, magnesium 2-octylmalonate, magnesium 2-heptylmalonate, magnesium 2-hexylmalonate, magnesium 2-pentylmalonate, magnesium 2-butylmalonate, magnesium 2-propylmalonate, magnesium 2-ethylmalonate, magnesium 2-methylmalonate, magnesium 2-phenylmalonate, magnesium 2-(p-tolyl)malonate, magnesium 2-mesitylmalonate, magnesium 2-(4-(tert-butyl)phenyl)malonate, magnesium 2-(4-(tert-butyl)-2-methylphenyl)malonate, magnesium 2-(4-(tert-butyl)-2,6-dimethylphenyl)malonate, magnesium 2,2-diphenylmalonate, magnesium 2-methyl-2-phenylmalonate, magnesium 2-ethyl-2-phenylmalonate, magnesium 2-phenyl-2-propylmalonate, magnesium 2-butyl-2-phenylmalonate, magnesium 2-pentyl-2-phenylmalonate, magnesium 2-hexyl-2-phenylmalonate, magnesium 2-heptyl-2-phenylmalonate, magnesium 2-octyl-2-phenylmalonate, magnesium 2-nonyl-2-phenylmalonate, magnesium 2-decyl-2-phenylmalonate, magnesium 2-phenyl-2-undecylmalonate, magnesium 2-dodecyl-2-phenylmalonate, magnesium 2-isopropyl-2-methylmalonate, magnesium 2,2-diisopropylmalonate, magnesium 2-isopropylmalonate, magnesium 2-(tert-butyl)malonate, magnesium 2-ditert-butylmalonate, magnesium 2-(tert-butyl)-2-methylmalonate, magnesium 2-(tert-butyl)-2-ethylmalonate, magnesium 2-ethyl-2-isopropylmalonate, magnesium 2-isopropyl-2-propylmalonate, magnesium 2-butyl-2-isopropylmalonate, magnesium 2-isopropyl-2-pentylmalonate, magnesium 2-hexyl-2-isopropylmalonate, magnesium 2-heptyl-2-isopropylmalonate, magnesium 2-isopropyl-2-octylmalonate, magnesium 2-isopropyl-2-nonylmalonate, magnesium 2-decyl-2-isopropylmalonate, magnesium 2-isopropyl-2-undecylmalonate, magnesium 2-(tert-butyl)-2-undecylmalonate, magnesium 2-(tert-butyl)-2-decylmalonate, magnesium 2-(tert-butyl)-2-nonylmalonate, magnesium 2-(tert-butyl)-2-octylmalonate, magnesium 2-(tert-butyl)-2-heptylmalonate, magnesium 2-(tert-butyl)-2-hexylmalonate, magnesium 2-(tert-butyl)-2-pentylmalonate, magnesium 2-(tert-butyl)-2-butylmalonate, magnesium 2-(tert-butyl)-2-propylmalonate, magnesium 2-(tert-butyl)-2-ethylmalonate, magnesium 2-(tert-butyl)-2-phenylmalonate, magnesium 2-isopropyl-2-phenylmalonate, magnesium 2-(sec-butyl)malonate, magnesium 2-(sec-butyl)-2-methylmalonate, magnesium 2-methyl-2-(pentan-2-yl)malonate, magnesium 2-(hexan-2-yl)-2-methylmalonate, magnesium 2-(heptan-2-yl)-2-methylmalonate, magnesium 2-methyl-2-(octan-2-yl)malonate, magnesium 2-methyl-2-(nonan-2-yl)malonate, magnesium 2-methyl-2-(octan-3-yl)malonate, magnesium 2-(octan-3-yl)-2-octylmalonate, magnesium 2-benzyl-2-methylmalonate, magnesium 2,2-dibenzylmalonate, magnesium 2-benzyl-2-ethylmalonate, magnesium 2-benzyl-2-isopropylmalonate, magnesium 2-benzyl-2-(tert-butyl)malonate, magnesium 2-cyclohexylmalonate, magnesium 2-cyclohexyl-2-methylmalonate, magnesium 2-cyclohexyl-2-ethylmalonate, magnesium 2-cyclohexyl-2-isopropylmalonate, magnesium 2-(tert-butyl)-2-cyclohexylmalonate, magnesium 2,2-dicyclohexylmalonate, magnesium 2-cyclohexyl-2-(pentan-3-yl)malonate, magnesium 2-ethylmalonate, magnesium 2-isopropylmalonate, magnesium 2-(tert-butyl)malonate, magnesium 2-propylmalonate, magnesium 2-butylmalonate, magnesium 2-pentylmalonate, magnesium 2-(2-methylpentyl)malonate, magnesium 2-(2-ethylpentyl)malonate, magnesium 2-(3-ethylhexan-2-yl)malonate, magnesium 2-hexylmalonate, magnesium 2-heptylmalonate, magnesium 2-octylmalonate, magnesium 2-nonylmalonate, magnesium 2-decylmalonate, magnesium 2-decyl-2-isopropylmalonate.

In one of the feature of the present invention, the compound of formula I is selected from the group consisting of calcium 2,2-di-methylmalonate, magnesium 2,2-di-methylmalonate, barium 2,2-di-methylmalonate, lithium 2,2-di-methylmalonate, calcium 2,2-di-ethylmalonate, calcium 2-ethylmalonate, calcium 2-benzyl malonate, and calcium 2-methylmalonate.

According to the further feature, the present invention also encompasses metal stearates conforming to formula (II),

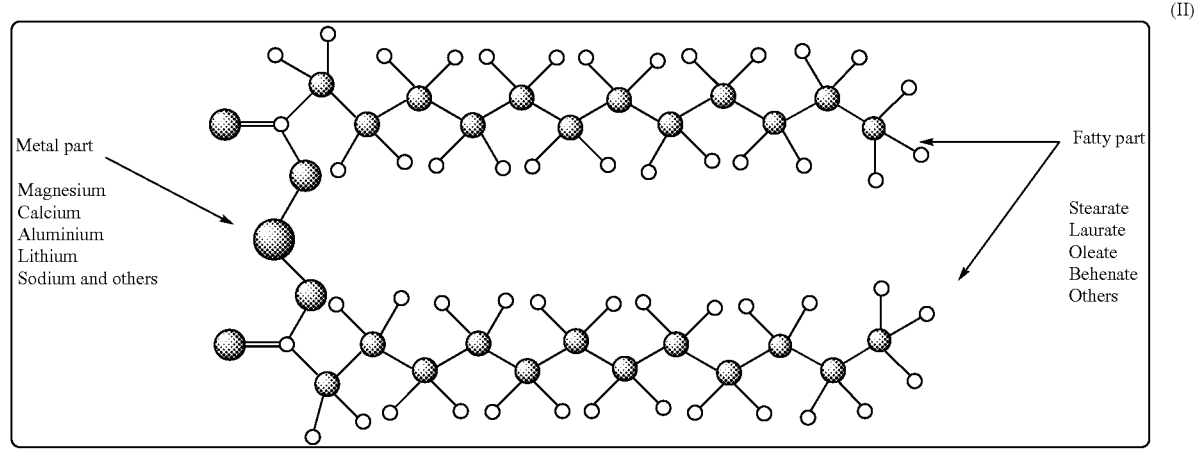

(II)

In one of the feature of the present invention, the metal stearate is selected from divalent metal stearate having formula $C_{36}H_{70}MO_4$, monovalent metal stearate having formula $C_{18}H_{35}MO_2$, and trivalent metal stearate having formula $C_{54}H_{105}MO_6$, wherein M is a metal and selected from magnesium, calcium, aluminium, lithium, and sodium.

In another feature of the present invention, formula (II) is selected from calcium stearate ($C_{36}H_{70}CaO_4$), magnesium stearate ($C_{36}H_{70}MgO_4$), lithium stearate ($C_{18}H_{35}LiO_2$), zinc stearate ($C_{36}H_{70}ZnO_4$), sodium stearate ($C_{18}H_{35}NaO_2$), and barium stearate ($C_{36}H_{70}BaO_4$).

According to the further feature, the present invention also encompasses metal oxides conforming to formula (III).

$$MO \qquad (III)$$

wherein:
M can be trivalent metal cation of aluminium and similar; divalent metal cation of calcium, magnesium and similar; monobasic metal cation of sodium and similar. O represents oxide. In one of the feature of the present invention, formula (III) is selected from calcium oxide, magnesium oxide, lithium oxide, barium oxide, sodium oxide, aluminium oxide, potassium oxide, iron oxide, and zinc oxide.

In preferred feature of the present invention, the metal stearate or metal oxide is added individually or as a mixture in the formulation with the above mentioned nucleator in an amount from about 1.0 percent to 90.0 percent by weight, in order to achieve desired results or characteristics. More preferably, the metal stearate or metal oxide is added individually or as a mixture in the formulation with the above mentioned nucleator in an amount from about 5.0 to about 70.0 percent by weight. Most preferably, the metal stearate or metal oxide is added individually or as a mixture in the formulation with the above mentioned nucleator in an amount from about 10.0 to 50.0 percent by weight.

The inventive metal salts of malonic acid derivatives are thus added within the target thermoplastic in an amount from about 0.005 percent to 2.0 percent by weight in order to achieve desired results or characteristics. More preferably, metal salts of malonic acid derivatives are added within the target thermoplastic in an amount from about 0.01 to about 1.5 percent by weight. Most preferably, metal salts of malonic acid derivatives are added within the target thermoplastic in an amount from about 0.02 to 1.0 percent by weight.

Metal salts of malonic acid derivatives may also be added in a polymer formulation in form of master-batch where it is desirable to include up to 50% or more of the active compound in a master-batch, although this is not a restriction.

Within the formulation or the final thermoplastic article made containing metal salts of malonic acid derivatives, other additives may be included like antioxidant, antimicrobial agent, acid scavengers, antistatic compounds, chlorine scavengers, dispersing aids, stabilizers, ultraviolet absorbers, and other similar standard thermoplastic additives. These co-additives along with metal salts of malonic acid derivatives may be present as admixture in powder, liquid, or in compressed/pellet form for easy feeding.

In one of the feature of the present invention, the antioxidant is selected from pentaerthrityl-tetrakis(3-(3,5'-di-tert-butyl-4-hydroxyphenyl)-propionate and tris(2,4-di-t-butyl-phenyl) phosphate.

In another feature of the present invention, the antimicrobial agent is selected from 10,10'-oxybisphenoxarsine and n-octyl-isothiazolinone.

In yet another feature of the present invention, the acid scavenger is selected from calcium stearates, hydrotalcites ($Mg_4Al_2(OH)_{12}CO_3.nH_2O$) and $Mg_6Al_2$ $(OH)_{16}CO_3.4H_2O$ (supplied asDHT-4A, Kisuma). In one of the preferred feature of the present invention, the acid scavenger is $Mg_6Al_2$ $(OH)_{16}CO_3.4H_2O$.

In yet another feature of the present invention, the antistatic compounds is selected from glycerol monostearate, and ethoxylated fatty acid amines.

In yet another feature of the present invention, the dispersing aid is selected from polyolefin waxes, mineral oils, and stearate esters of glycerin.

The compound thus obtained in accordance with the present invention may be added to polyolefin resin or formulation comprised of at least one semi crystalline polyolefin resin preferred examples include isotactic and syndiotactic polypropylene, polyethylene, poly(4-methyl-1-pentene), polybutylene, and any blends or copolymers thereof, whether high or low density in composition. The polyolefin polymers of the present invention may include aliphatic polyolefins and copolymers made from at least one aliphatic olefin and one or more ethylenically unsaturated co-monomers. Other polymers or rubber (such as ethylene propylene diene monomer (EPDM) or ethylene propylene rubber (EPR)) may also be compounded with the polyolefin.

Other co-monomer examples include acrylic acid and vinyl acetate, etc. Formulation may include polymer such as polyethylene terephthalate (PET), polybutylene terephthalate (PBT), and polyethylene naphthalate (PEN), as well as polyamides such as Nylon 6, Nylon 66, and others.

The present invention also provides a process for preparing a metal salt of malonic acid derivative, wherein the process comprising adding a malonic acid derivative in water and metal hydroxide to obtain a reaction mixture slurry and then heating the reaction mixture slurry to a temperature in the range of 20° C. to 120° C. along with continuous stirring for 5 min. to 10 hours to obtain a metal salt of malonic acid derivative.

The present invention also provides a polymer additive comprising:
(i) a component selected from metal stearate, metal oxide, and mixture thereof; and
(ii) the metal salt of malonic acid derivative compound having chemical Formula (I),
wherein the component (i) is present in an amount of from 1.0 percent to 90.0 percent by weight based on the total amount of the polymer additive.

In one of the feature of the polymer additive of the present invention, the metal stearate is selected from the group comprising of divalent metal stearate having formula $C_{36}H_{70}MO_4$, monovalent metal stearate having formula $C_{18}H_{35}MO_2$, and trivalent metal stearate having formula $C_{54}H_{105}MO_6$, wherein M is a metal and selected from magnesium, calcium, aluminium, lithium, and sodium.

In one of the feature of the polymer additive of the present invention, the metal oxides conforming to formula (III)

MO      (III)

wherein M is selected from trivalent metal cation, divalent metal cation, and monobasic metal cation and O is oxide.

The present invention also provides a thermoplastic composition comprising;
(i) a polyolefin resin or polyolefin formulation; and
(ii) the metal salt of malonic acid derivative compound having chemical formula (I),
wherein the metal salt of malonic acid derivative is present in an amount from 0.005 percent to 2.0 percent by weight based on the amount of the thermoplastic composition.

In one of the feature of the present invention, the thermoplastic composition optionally comprising the metal stearate and the metal stearate is selected from the group comprising of divalent metal stearate having formula $C_{36}H_{70}MO_4$, monovalent metal stearate having formula $C_{18}H_{35}MO_2$, and trivalent metal stearate having formula $C_{54}H_{105}MO_6$, wherein M is a metal and selected from magnesium, calcium, aluminium, lithium, and sodium.

In another feature of the present invention, the thermoplastic composition optionally comprising the metal oxide conforming to formula (III)

MO      (III)

wherein M is selected from trivalent metal cation, divalent metal cation, and monobasic metal cation and O is oxide.

In one of the feature of the thermoplastic composition of the present invention, the polyolefin resin or polyolefin formulation comprises at least one semi crystalline polyolefin resin.

In another feature of the present invention, the thermoplastic composition optionally comprising antioxidant, antimicrobial agent, acid scavenger, antistatic compound, chlorine scavenger, dispersing aid, stabilizer, ultraviolet absorber, and other similar standard thermoplastic additive.

Generally, any thermoplastic composition having some degree of crystalline content may be improved with the nucleating agents of the present invention.

The following non-limiting examples illustrate in details about the invention. However, they are not intended to be limiting the scope of present invention in any way.

General Synthesis Procedure of Metal Salt of Malonic Acid Derivative

In a 2-neck flask with equipped with magnetic stirrer and was added malonic acid derivative in distilled water and metal hydroxide was added to the reaction mixture and then reaction mixture slurry was heated to 70° C. The stirring was continued for 5 hours. The white product was collected by suction filtration, washed thrice with water, and dried in a vacuum oven overnight at 90° C.

Example-1

General Synthesis Procedure of Calcium Salt of di-methyl malonic Acid (Calcium 2,2-di-methylmalonate)

To a 500 mL 2-neck flask with equipped with magnetic stirrer and was added di-methylmalonic acid (5.0 g, 0.037 mol) in 250 ml of distilled water and calcium hydroxide (2.8 g, 0.038 mol) was added to the reaction mixture and then reaction mixture slurry was heated to 70° C. The stirring was continued for 5 hours, the mixture became quite thick, at which time the pH of the aqueous phase was found to be about 7. The white product was collected by suction filtration, washed thrice with water, and dried in a vacuum oven overnight at 90° C. Yield 98%.

Example-2

General Synthesis Procedure of Magnesium Salt of di-methyl malonic Acid (Magnesium 2,2-di-methylmalonate)

To a 500 mL 2-neck flask with equipped with magnetic stirrer and was added di-methylmalonic acid (5.0 g, 0.037 mol) in 250 ml of distilled water and magnesium hydroxide (2.16 g, 0.038 mol) was added to the reaction mixture and then reaction mixture slurry was heated to 70° C. The stirring was continued for another 5 hours, the solvent was removed from rotoevaporator. After removal of the solvent, the final product obtained as white powder and dried in a vacuum oven overnight at 90° C. Yield 99%.

Example-3

General Synthesis Procedure of Barium Salt of di-methyl malonic Acid (Barium 2,2-di-methylmalonate)

To a 500 mL 2-neck flask with equipped with magnetic stirrer and was added di-methylmalonic acid (5.0 g, 0.037 mol) in 250 ml of distilled water and barium hydroxide octahydrate (11.93 g, 0.038 mol) was added to the reaction mixture and then reaction mixture slurry was heated to 70° C. The stirring was continued for 5 hours, the mixture became quite thick, at which time the pH of the aqueous phase was found to be about 7. The white product was collected by suction filtration, washed thrice with water, and dried in a vacuum oven overnight at 90° C. Yield 95%.

Example-4

General Synthesis Procedure of Lithium Salt of di-methyl malonic Acid (Lithium 2,2-di-methylmalonate)

To a 500 mL 2-neck flask with equipped with magnetic stirrer and was added di-methyl malonic acid (5.0 g, 0.037 mol) in 250 ml of distilled water and lithium hydroxide monohydrate (3.18 g, 0.075 mol) was added to the reaction mixture and then reaction mixture slurry was heated to 70° C. The stirring was continued for another 5 hours, the solvent was removed from rotoevaporator. After removal of the solvent, the final product obtained as white powder and dried in a vacuum oven overnight at 90° C. Yield 95%.

Example-5

General Synthesis Procedure of Calcium Salt of Malonic Acid (Comparative)

To a 500 mL 2-neck flask with equipped with magnetic stirrer and was added malonic acid (5.0 g, 0.048 mol) in 250 ml of distilled water and calcium hydroxide (3.55 g, 0.048 mol) was added to the reaction mixture and then reaction mixture slurry was heated to 70° C. The stirring was continued for 5 hours, the mixture became quite thick, at which time the pH of the aqueous phase was found to be about 7. The white product was collected by suction filtration, washed thrice with water, and dried in a vacuum oven overnight at 90° C. Yield 98%.

Example-6

General Synthesis Procedure of Magnesium Salt of Malonic Acid (Comparative)

To a 500 mL 2-neck flask with equipped with magnetic stirrer and was added malonic acid (5.0 g, 0.048 mol) in 250 ml of distilled water and magnesium hydroxide (2.8 g, 0.048 mol) was added to the reaction mixture and then reaction mixture slurry was heated to 70° C. The stirring was continued for another 5 hours at 70° C., the solvent was removed from rotoevaporator. After removal of the solvent, the final product obtained as white powder and dried in a vacuum oven overnight at 90° C. Yield 99%.

Example-7

General Synthesis Procedure of Reaction Between Calcium Salt of Malonic Acid and Pimelic Acid (Comparative)

In a 250 mL 2-neck flask with equipped with magnetic stirrer and pimelic acid (dicarboxylic acid) 5.0 g was added in 50 ml of acetone and stirred for 1 hours to obtain clear solution. 5.0 g of calcium salt of malonic acid (5.0 g) was added to the solution and then reaction mixture slurry was heated to 40° C. The stirring was continued for 5 hours, the mixture became milky. The white product was collected by suction filtration, washed thrice with acetone to remove unreacted pimelic acid, and dried in a vacuum oven overnight at 90° C.

Example-8

General Synthesis Procedure of Reaction Between Calcium Salt of di-methyl Malonic Acid and Pimelic Acid (Comparative)

In a 250 mL 2-neck flask with equipped with magnetic stirrer and pimelic acid (dicarboxylic acid) 5.0 g was added in 50 ml of acetone and stirred for 1 hours to obtain clear solution. 5.0 g of calcium salt of di-methyl malonic acid (5.0 g) was added to the solution and then reaction mixture slurry was heated to 40° C. The stirring was continued for 5 hours, the mixture became milky. The white product was collected by suction filtration, washed thrice with acetone to remove unreacted pimelic acid, and dried in a vacuum oven overnight at 90° C.

Example-9

General Synthesis Procedure of Calcium Salt of di-ethyl Malonic Acid (Calcium 2,2-di-ethylmalonate)

To a 500 mL 2-neck flask with equipped with magnetic stirrer and was added di-ethyl malonic acid (4.0 g, 0.025 mol) in 200 ml of distilled water and calcium hydroxide (1.85 g, 0.025 mol) was added to the reaction mixture and then reaction mixture slurry was heated to 70° C. The stirring was continued for 5 hours, the mixture became quite thick, at which time the pH of the aqueous phase was found to be about 7. The white product was collected by suction filtration, washed thrice with water, and dried in a vacuum oven overnight at 90° C. Yield 95%.

Example-10

General Synthesis Procedure of Calcium Salt of Ethyl Malonic Acid (Calcium 2-ethylmalonate)

To a 500 mL 2-neck flask with equipped with magnetic stirrer and was added ethyl malonic acid (1.5 g, 0.0114 mol) in 100 ml of distilled water and calcium hydroxide (0.85 g, 0.0114 mol) was added to the reaction mixture and then reaction mixture slurry was heated to 70° C. The stirring was continued for another 5 hours. The solvent was removed from rotoevaporator. After removal of the solvent, the final product obtained as white powder and dried in a vacuum oven overnight at 90° C. Yield 95%.

Example-11

General Synthesis Procedure of Calcium Salt of Benzyl Malonic Acid (Calcium 2-benzyl malonate)

To a 500 mL 2-neck flask with equipped with magnetic stirrer and was added benzyl malonic acid (2.0 g, 0.010 mol) in 100 ml of distilled water and calcium hydroxide (0.76 g, 0.010 mol) was added to the reaction mixture and then reaction mixture slurry was heated to 70° C. The stirring was continued for another 5 hours. The solvent was removed from rotoevaporator. After removal of the solvent, the final product obtained as white powder and dried in a vacuum oven overnight at 90° C. Yield 95%.

Example-12

General Synthesis Procedure of Calcium Salt of Methyl Malonic Acid (Calcium 2-methylmalonate)

To a 500 mL 2-neck flask with equipped with magnetic stirrer and was added methyl malonic acid (3.0 g, 0.0254 mol) in 150 ml of distilled water and calcium hydroxide (1.88 g, 0.0254 mol) was added to the reaction mixture and then reaction mixture slurry was heated to 70° C. The stirring was continued for another 5 hours, the mixture became quite thick, at which time the pH of the aqueous phase was found to be about 7. The white product was collected by suction filtration, washed thrice with water, and dried in a vacuum oven overnight at 90° C. Yield 95%.

Recipes:

All the mixtures were prepared of batch size of 2000 g (2 Kg), polypropylene was 1996.65 g whereas rest amounts constitutes all the additives (antioxidants, acid scavenger and metal salt of malonic acid derivates). Prior to extrusion, polymer and additives were homogeneous mixed using high speed mixer for 2 minutes. Mixtures 1-8 were prepared using polypropylene homopolymer (PP-HP) having WI (15 g/10 min) mixed with 0.35% pentaerthrityl-tetrakis(3-(3',5'-di-tert-butyl-4-hydroxyphenyl)-propionate (supplied as Irganox 1010, Ciba SC), 0.70% tris(2,4-di-t-butyl-phenyl) phosphate (supplied as Irgafos 168, Ciba SC) and 0.375% calcium stearate (CaSt). In mixture 3, 0.375% of $(Mg_6Al_2(OH)_{16}CO_3 \cdot 4H_2O)$ (supplied as DHT-4A, Kisuma) was added instead of calcium stearate. DHT-4A or calcium stearates are commonly used as acid scavengers in polyolefins. Various metal salts of malonic acid derivatives were added as in mixture 2-6 (synthesized as per procedure described above). Mixtures 7-8 were prepared for comparative purpose containing commercial nucleating agents HPN-20E (metal salt of Hexahydropthalic acid, supplied by Milliken Corporation) and sodium benzoate (NaBz) used in polyolefin industry. Mixtures 1-8 were extruded using a extruder (M/s. Labtech make twin screw extruder) at a melt temperature of 230° C. and injection molded at 230° C. (M/s. Toshiba Machine (India) Pvt. Ltd. make ASWA Injection molding machine). The obtained products were evaluated for their thermal-mechanical properties. Injection molded specimens were conditioned for 48 hrs at 55° C. and 23° C. prior to testing.

EXPERIMENTAL TABLE 1

Inventive Nucleator performance in Homo polypropylene (15 MFI) @ 1000 ppm concentration

| Mixture No. | Nucleator added (Example No. from above) | Nucleator Dosage | Acid scavenger | Haze (%) | Tc (° C.) | $Tm_\alpha$ (° C.) | Flexural modulus (Mpa) | Flexural modulus (std. dev.) |
|---|---|---|---|---|---|---|---|---|
| 1 | PP | — | CaSt | 94.5 | 121.5 | 165.2 | 1220 | 18 |
| 2 | 1 | 1000 | CaSt | 72.1 | 131.8 | 166.3 | 1526 | 25 |
| 3 | 1 | 1000 | DHT-4A | 66.4 | 132.0 | 166.6 | 1557 | 13 |
| 4 | 2 | 1000 | CaSt | 78.8 | 130.0 | 165.8 | 1460 | 22 |
| 5 | 3 | 1000 | CaSt | 81.8 | 127.2 | 167.1 | 1379 | 07 |
| 6 | 4 | 1000 | CaSt | 73.7 | 130.3 | 165.8 | 1509 | 23 |
| 7 | HPN-20E | 1000 | CaSt | 73.8 | 129.4 | 167.0 | 1454 | 20 |
| 8 | NaBz | 1000 | CaSt | 82.4 | 127.1 | 166.0 | 1374 | 13 |

From table above, inventive salts of malonic acid derivatives (mixture 2-4 & 6), exhibited higher peak crystallization temperature and flexural modulus. The haze values were relatively on lower side as compared to commercial nucleator sodium benzoate (NaBz). Thus the metal salts of malonic acid derivatives acts as effective α-nucleating agents.

Mixtures 9-13 were prepared using polypropylene homopolymer (PP-HP) having MFI (15 g/10 min) mixed with 0.35% pentaerthrityl-tetrakis(3-(3',5'-di-tert-butyl-4-hydroxyphenyl)-propionate (supplied as Irganox 1010, Ciba SC), 0.70% tris(2,4-di-t-butyl-phenyl) phosphate (supplied as Irgafos 168, Ciba SC) and 0.375% calcium stearate (CaSt). 2000 ppm of Calcium salt of di-methyl malonic acid (derivate of malonic acid) was added as part of mixture 10-11. Mixtures 12-13 were prepared for comparative purpose containing commercial nucleating agents used in polyolefin industry (HPN-20E and NA-27 supplied by M/s. Milliken Corporation and M/s. Adeka Corporation). In mixture 11, 0.375% of $(Mg_6Al_2(OH)_{16}CO_3 \cdot 4H_2O)$ (supplied as DHT-4A, Kisuma) was added instead of calcium stearate.

EXPERIMENTAL TABLE 2

Inventive Nucleator performance in Homo polypropylene (15 MFI) @ 2000 ppm concentration

| Mixture No. | Nucleator added (Example No. from above) | Nucleator Dosage (ppm) | Acid scavenger | Tc (° C.) | $Tm_\alpha$ (° C.) |
|---|---|---|---|---|---|
| 9 | PP | — | CaSt | 121.5 | 165.2 |
| 10 | 1 | 2000 | CaSt | 133.1 | 165.4 |
| 11 | 1 | 2000 | DHT-4A | 131.5 | 166.5 |
| 12 | HPN-20E | 2000 | CaSt | 128.1 | 165.7 |
| 13 | NA-27 | 2000 | CaSt | 130.9 | 166.5 |

The peak crystallization temperature of polypropylene nucleated with inventive compound was found to be higher as compared to the commercial α-nucleating agents. Higher crystallization temperature corresponds to lower cycle time and higher productivity during molding or any other related process.

Mixtures 14-17 were prepared using polypropylene homopolymer (PP-HP) having MFI (15 g/10 min) mixed with 0.35% pentaerthrityl-tetrakis(3-(3',5'-di-tert-butyl-4-hydroxyphenyl)-propionate (supplied as Irganox 1010, Ciba SC), 0.70% tris(2,4-di-t-butyl-phenyl) phosphate (supplied as Irgafos 168, Ciba SC) and 0.375% calcium stearate (CaSt) containing calcium salt of different malonic acid derivatives. 2000 ppm of each inventive compound were added as part of each formulation. The peak crystallization temperature of polypropylene increased significantly when nucleated with inventive metal salts as mentioned in table-3.

EXPERIMENTAL TABLE 3

Inventive Nucleator performance (metal salts of other malonic acid derivatives) in Homo polypropylene (15 MFI) @ 2000 ppm concentration

| Mixture No. | Nucleator added (Example No. from above) | Nucleator Dosage (ppm) | Acid scavenger | Tc (° C.) | $Tm_\alpha$ (° C.) |
|---|---|---|---|---|---|
| 14 | 9 | 2000 | CaSt | 132.1 | 165.1 |
| 15 | 10 | 2000 | CaSt | 126.1 | 165.5 |
| 16 | 11 | 2000 | CaSt | 126.7 | 164.6 |
| 17 | 12 | 2000 | CaSt | 126.7 | 165.4 |

Mixtures 18-20 were prepared using polypropylene homopolymer (PP-HP) having MFI (03 g/10 min) mixed with 0.35% pentaerthrityl-tetrakis(3-(3,5'-di-tert-butyl-4-hydroxyphenyl)-propionate (supplied as Irganox 1010, Ciba SC), 0.70% tris(2,4-di-t-butyl-phenyl) phosphate (supplied as Irgafos 168, Ciba SC) and 0.375% calcium stearate (CaSt). Calcium salt of di-methyl malonic acid was varied as 250 ppm, 500 ppm and 1000 ppm in respective mixtures as mentioned in table-4.

EXPERIMENTAL TABLE 4

Inventive Nucleator performance in Homo polypropylene (03 MFI) @ 2000 ppm concentration

| Mixture No. | Nucleator added (Example No. from above) | Nucleator Dosage (ppm) | Acid scavenger | Tc (° C.) | $Tm_\alpha$ (° C.) |
|---|---|---|---|---|---|
| 18 | 1 | 250 | CaSt | 132.0 | 166.2 |
| 19 | 1 | 500 | CaSt | 132.2 | 165.7 |
| 20 | 1 | 1000 | CaSt | 133.1 | 165.3 |

The significant increase in the peak crystallization temperature of polypropylene having 03 MFI nucleated with varying concentration of inventive compound shows effectiveness as good α-nucleating agent.

Mixtures 21-27 were prepared using polypropylene homopolymer (PP-HP) having MFI (15 g/10 min) mixed with 0.35% pentaerthrityl-tetrakis(3-(3,5'-di-tert-butyl-4-hydroxyphenyl)-propionate (supplied as Irganox 1010, Ciba SC), 0.70% tris(2,4-di-t-butyl-phenyl) phosphate (supplied as Irgafos 168, Ciba SC) and 0.375% calcium stearate (CaSt). 250 ppm of Calcium salt of di-methyl malonic acid was added as part of each mixture 21-27. Zinc stearate (metal stearate) and Zinc oxide (metal oxide) were varied as 10% to 30% as mentioned in table-5 below. Mixture 27 contain 50% each of zinc stearate and zinc oxide by wt. % of total 30%.

EXPERIMENTAL TABLE 5

Inventive Nucleator performance (metal salts of malonic acid derivatives containing metal stearates and oxides) in Homo polypropylene (15 MFI) @ 250 ppm concentration

| Mixture No. | Nucleator added (Example No. from above) | Nucleator Dosage (ppm) | Acid scavenger | Metal stearate/ oxide (%) | Tc (° C.) | $Tm_\alpha$ (° C.) |
|---|---|---|---|---|---|---|
| 21 | 1 | 250 | CaSt | ZnSt (10%) | 132.3 | 167.5 |
| 22 | 1 | 250 | CaSt | ZnSt (20%) | 131.6 | 166.7 |
| 23 | 1 | 250 | CaSt | ZnSt (30%) | 132.4 | 167.6 |
| 24 | 1 | 250 | CaSt | ZnO (10%) | 132.4 | 168.3 |
| 25 | 1 | 250 | CaSt | ZnO (20%) | 132.2 | 167.3 |
| 26 | 1 | 250 | CaSt | ZnO (30%) | 132.5 | 167.6 |
| 27 | 1 | 250 | CaSt | ZnO: 50%::50% ZnSt (30%) | 131.3 | 166.8 |

From table-5, with addition of metal stearate or metal oxide or their blend as part of the inventive compound concentration in polymer does not hinder the nucleation ability of the inventive compounds but acts as a dispersing agent.

Mixtures 28-32 were prepared for comparison purpose using polypropylene homopolymer (PP-HP) having MFI (15 g/10 min) mixed with 0.35% pentaerthrityl-tetrakis(3-(3',5'-di-tert-butyl-4-hydroxyphenyl)-propionate (supplied as Irganox 1010, Ciba SC), 0.70% tris(2,4-di-t-butyl-phenyl) phosphate (supplied as Irgafos 168, Ciba SC) and 0.375% calcium stearate (CaSt) containing 1000 ppm of calcium salt of different compounds as mentioned in table-6.

COMPARATIVE EXPERIMENTAL TABLE 6

Nucleator performance in Homo polypropylene (15 MFI) @ 1000 ppm concentration

| Mixture No. | Nucleator added (Example No. from above) | Nucleator Dosage (ppm) | Acid scavenger | Haze (%) | Tc (° C.) | Tm$_\alpha$ (° C.) | Flexural modulus (Mpa) | Flexural modulus (std. dev.) |
|---|---|---|---|---|---|---|---|---|
| 28 | PP | — | CaSt | 94.5 | 121.5 | 165.2 | 1220 | 18 |
| 29 | 5 | 1000 | CaSt | 88.7 | 126.0 | 166.4 | 1193 | 10 |
| 30 | 6 | 1000 | CaSt | 96.3 | 123.1 | 166.0 | 1082 | 19 |
| 31 | 7 | 1000 | CaSt | — | 125.1 | 165.6 | — | — |
| 32 | 8 | 1000 | CaSt | — | 129.4 | 165.1 | — | — |

As reported in J. Macromolecular science, Part B: Physics (47:900-912,2008), various metal salts of malonic acid acts as β-nucleating agent at 3000 ppm (0.3%) concentration in polypropylene matrix however the compounds 5-6 (calcium and magnesium salt of malonic acid, table-6) at 1000 ppm did not show any beta nucleation effect. No significant increase in flexural modulus and peak crystallization temperature was observed. The reason may be due to lower concentration being used or lower extrusion time as it was 2 min as mentioned in the research article. Calcium salts of malonic and di-methyl malonic acid were reacted with di-carboxylic acid (synthesis procedure described above). No beta nucleation effect was observed in polypropylene however there was improvement in the peak crystallization temperature (Tm$_\alpha$).

Two gram of each compound as mentioned in table-7 were vacuum dried for 12 hrs and later placed in humidity chamber set at 60% for 05 days. Compounds were evenly spread on watch glass to give maximum surface area for moisture intake. Weight gained is reported as % moisture uptake in 05 days.

EXPERIMENTAL TABLE 7

Hygroscopicity of Compounds

| Mixture No. | Nucleator added (Example No. from above) | % Water absorbed |
|---|---|---|
| 33 | 1 | 0.37 |
| 34 | NaBz (comparative) | 0.83 |

From table-7, it is clear that the inventive compound showed lower hygroscopicity.

A mixture 36 containing 5000 ppm of calcium salt of di-methyl malonic acid was prepared for comparison purpose using Nylon-6 supplied by UBE industries (Grade-101-3B).

EXPERIMENTAL TABLE 8

Inventive Nucleator performance in Nylon-6 @ 5000 ppm concentration

| Mixture No. above) | Nucleator added (Example No. from | Nucleator Dosage (ppm) | Tc (° C.) | Tm$_\alpha$ (° C.) |
|---|---|---|---|---|
| 35 | Nylon-6 | — | 169.4 | 220.5 |
| 36 | 1 | 5000 | 188.0 | 220.7 |

Nylon-6 nucleated with the inventive compound exhibited significant increase in peak crystallization temperature as compared to non-nucleated Nylon-6.

From the inventive examples it has been found and confirmed that metal salts of malonic acid derivatives acts as efficient α-nucleating agent or Nucleator thereby increasing peak crystallization temperature by several degrees and flexural modulus and lower haze.

Abbreviations

PP Polypropylene
PP-HP Polypropylene Homopolymer
DMMA Di-Methyl malonic acid
MFI Melt flow index/rate
Tm Melting temperature
Tc Crystallization temperature
NaBz Sodium Benzoate
9999ZnSt Zinc stearate
ZnO Zinc Oxide
CaSt Calcium stearate

We claim:

1. A metal salt of malonic acid derivative compound having formula (I):

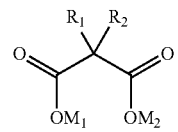

wherein:
each of $R_1$ and $R_2$ groups are alkyl groups having 2 carbon atoms;
each of $M_1$ and $M_2$ are selected from monovalent metal and divalent metal; and
wherein the compound of formula I is selected from a group consisting of lithium 2,2-diethylmalonate, barium 2,2-diethylmalonate, calcium 2,2-diethylmalonate, and magnesium 2,2-diethylmalonate.

2. A process for preparing a metal salt of malonic acid derivative as claimed in claim 1, wherein the process comprising adding a malonic acid derivative in water and metal hydroxide to obtain a reaction mixture slurry and then heating the reaction mixture slurry to a temperature in the range of 20° C. to 120° C. along with continuous stirring for 5 min. to 10 hours to obtain a metal salt of malonic acid derivative.

3. A polymer additive comprising:
(i) a component selected from metal stearate, metal oxide, and mixture thereof;
(ii) the metal salt of malonic acid derivative compound having chemical Formula (I) as claimed in claim 1;
wherein the component (i) is present in an amount of from 1.0 percent to 90.0 percent by weight based on the total amount of the polymer additive.

4. The polymer additive as claimed in claim 3, wherein the metal stearate is selected from the group comprising of divalent metal stearate having formula $C_{36}H_{70}MO_4$, monovalent metal stearate having formula $C_{18}H_{35}MO_2$, and trivalent metal stearate having formula $C_{54}H_{105}MO_6$, wherein M is a metal and selected from magnesium, calcium, aluminium, lithium, and sodium.

5. The polymer additive as claimed in claim 3, wherein the metal oxides conforming to formula (III)

$$MO \qquad\qquad (III)$$

wherein M is selected from trivalent metal cation, divalent metal cation, and monobasic metal cation.

6. A thermoplastic composition comprising;
(i) a polyolefin resin or polyolefin formulation; and
(ii) the metal salt of malonic acid derivative compound having chemical Formula (I) as claimed in claim 1,
wherein the metal salt of malonic acid derivative is present in an amount from 0.005 percent to 2.0 percent by weight based on the amount of the thermoplastic composition.

7. The thermoplastic composition as claimed in claim 6, optionally comprising the metal stearate and the metal stearate is selected from the group comprising of divalent metal stearate having formula $C_{36}H_{70}MO_4$, monovalent metal stearate having formula $C_{18}H_{35}MO_2$, and trivalent metal stearate having formula $C_{54}H_{105}MO_6$, wherein M is a metal and selected from magnesium, calcium, aluminium, lithium, and sodium.

8. The thermoplastic composition as claimed in claim 6, optionally comprising the metal oxide conforming to formula (III)

$$MO \qquad\qquad (III)$$

wherein M is selected from trivalent metal cation, divalent metal cation, and monobasic metal cation.

9. The thermoplastic composition as claimed in claim 6, wherein the polyolefin resin or polyolefin formulation comprises at least one semi crystalline polyolefin resin.

10. The thermoplastic composition as claimed in claim 6, optionally comprising antioxidant, antimicrobial agent, acid scavenger, antistatic compound, chlorine scavenger, dispersing aid, stabilizer, ultraviolet absorber, and other similar standard thermoplastic additive.

* * * * *